(12) United States Patent
Weinkam et al.

(10) Patent No.: US 11,678,933 B2
(45) Date of Patent: Jun. 20, 2023

(54) INTRA-CARDIAC MAPPING AND ABLATING

(71) Applicant: Kardium Inc., Burnaby (CA)

(72) Inventors: Daniel Robert Weinkam, Coquitlam (CA); Jeffery Charles Brewster, Burnaby (CA)

(73) Assignee: KARDIUM INC., Burnaby (CA)

( * ) Notice: Subject to any disclaimer, the term of this patent is extended or adjusted under 35 U.S.C. 154(b) by 183 days.

(21) Appl. No.: 17/140,522

(22) Filed: Jan. 4, 2021

(65) Prior Publication Data

US 2021/0153934 A1    May 27, 2021

Related U.S. Application Data

(60) Division of application No. 16/380,325, filed on Apr. 10, 2019, now Pat. No. 10,918,438, which is a
(Continued)

(51) Int. Cl.
*A61B 5/00* (2006.01)
*A61B 18/14* (2006.01)
(Continued)

(52) U.S. Cl.
CPC ............ *A61B 18/1492* (2013.01); *A61B 5/01* (2013.01); *A61B 5/027* (2013.01); *A61B 5/06* (2013.01);
(Continued)

(58) Field of Classification Search
CPC ............ A61B 18/1206; A61B 18/1233; A61B 18/1492; A61B 2018/00267;
(Continued)

(56) References Cited

U.S. PATENT DOCUMENTS

| | | |
|---|---|---|
| 5,462,545 A | 10/1995 | Wang et al. |
| 5,971,980 A | 10/1999 | Sherman |

(Continued)

FOREIGN PATENT DOCUMENTS

| | | |
|---|---|---|
| WO | 9858681 A2 | 12/1998 |
| WO | 2010056771 A1 | 5/2010 |

(Continued)

OTHER PUBLICATIONS

Extended European Search Report issued in European Appln. No. 20196376.6 dated Jan. 15, 2021.
(Continued)

*Primary Examiner* — Rex R Holmes
(74) *Attorney, Agent, or Firm* — Rossi, Kimms & McDowell LLP

(57) ABSTRACT

Systems, methods, and devices allow percutaneous mapping, orientation and/or ablation in bodily cavities or lumens. Such may include a structure that is percutaneously positionable in a cavity, such as an intra-cardiac cavity of a heart. Transducers carried by the structure are responsive to blood flow. For example, the transducers may sense temperature, temperature being related to convective cooling caused by blood flow. A controller discerns positional information or location, based on signals from the transducers. For example, blood flow may be greater and/or faster proximate a port in cardiac tissue than proximate tissue spaced from the port. Position information may allow precise ablation of selected tissue, for example tissue surround a port in the intra-cardiac cavity.

22 Claims, 19 Drawing Sheets

Related U.S. Application Data continuation of application No. 15/007,594, filed on Jan. 27, 2016, now Pat. No. 10,350,003, which is a division of application No. 13/596,774, filed on Aug. 28, 2012, now Pat. No. 9,277,960.

(60) Provisional application No. 61/532,423, filed on Sep. 8, 2011.

(51) Int. Cl.
| | |
|---|---|
| *A61B 5/06* | (2006.01) |
| *A61B 5/01* | (2006.01) |
| *A61B 5/027* | (2006.01) |
| *A61B 18/12* | (2006.01) |
| *A61B 18/00* | (2006.01) |
| *A61B 17/00* | (2006.01) |

(52) U.S. Cl.
CPC ............ *A61B 5/065* (2013.01); *A61B 5/6858* (2013.01); *A61B 18/1206* (2013.01); *A61B 2017/00154* (2013.01); *A61B 2017/00199* (2013.01); *A61B 2018/0016* (2013.01); *A61B 2018/00267* (2013.01); *A61B 2018/00357* (2013.01); *A61B 2018/00577* (2013.01); *A61B 2018/00648* (2013.01); *A61B 2018/00797* (2013.01); *A61B 2018/00815* (2013.01); *A61B 2018/00863* (2013.01); *A61B 2018/1467* (2013.01)

(58) Field of Classification Search
CPC A61B 2018/00357; A61B 2018/00577; A61B 2018/00797; A61B 2018/00839; A61B 2018/00875; A61B 2018/00892; A61B 5/01; A61B 5/0422; A61B 5/053; A61B 5/0538; A61B 5/6858; A61B 5/6869; A61B 5/743; A61B 5/7435; A61N 1/362
See application file for complete search history.

(56) References Cited

U.S. PATENT DOCUMENTS

| | | | |
|---|---|---|---|
| 5,991,650 A | 11/1999 | Swanson et al. | |
| 6,023,638 A | 2/2000 | Swanson | |
| 6,045,550 A | 4/2000 | Simpson et al. | |
| 8,295,902 B2 | 10/2012 | Salahieh et al. | |
| 9,492,228 B2 | 11/2016 | Lopes et al. | |
| 10,350,003 B2 * | 7/2019 | Weinkam | A61B 5/027 |
| 2002/0087156 A1 | 7/2002 | Maguire et al. | |
| 2002/0123749 A1 | 9/2002 | Jain | |
| 2002/0161361 A1 | 10/2002 | Sherman et al. | |
| 2004/0260346 A1 | 12/2004 | Overall et al. | |
| 2008/0004534 A1 | 1/2008 | Gelbart et al. | |
| 2008/0183251 A1 | 7/2008 | Azar et al. | |
| 2009/0131930 A1 * | 5/2009 | Gelbart | A61B 5/06 606/41 |
| 2010/0179524 A1 | 7/2010 | Whayne | |
| 2012/0197243 A1 | 8/2012 | Sherman et al. | |
| 2013/0066220 A1 | 3/2013 | Weinkam et al. | |
| 2013/0190587 A1 | 7/2013 | Lopes et al. | |
| 2013/0310702 A1 | 11/2013 | Reinders et al. | |
| 2014/0276769 A1 | 9/2014 | Goertzen et al. | |
| 2017/0231683 A1 | 8/2017 | Weinkam et al. | |
| 2020/0030019 A1 | 1/2020 | Weinkam | |

FOREIGN PATENT DOCUMENTS

| | | |
|---|---|---|
| WO | 2012100184 A2 | 7/2012 |
| WO | 2012100185 A2 | 7/2012 |
| WO | 2016080965 A1 | 5/2016 |

OTHER PUBLICATIONS

"Constellation Mapping Catheters", Brochure, Boston Scientific Corp., 2 pgs, © 2007 Boston Scientific Corporation.
"Phased RF Catheter Ablation System", 2014 Medtronic Inc , 2 pgs, http://www.medtronic.eu/your-health/atrial-fibrillation/about-the-therapy/our-phased-rf-ablation-system/[Jun. 24, 2014 2:38:05 PM].
"ThermoCool® Irrigated Tip Catheter", Brochure, Biosense Webster, 4 pgs, Biosense Webster, Inc 3333 Diamond Canyon Road Diamond Bar, CA 91765, USA, © Biosense Webster, Inc. 2009 All rights reserved. 1109003.0.
BIOTRONIK'S "AlCath Flutter Gold Cath for Atrial Flutter Available in EU", medGadget, 3 pgs, http://www.medgadget.com/2013/09/biotroniks-alcath-flutter-gold-cath-for-atrial-flutter-unveiled-in-europe.html[Jun. 24, 2014 2:37:09 PM].
Invitation to Pay Additional Fees and, Where Applicable, Protest Fee issued in Intl. Appln. No. PCT/US2014/066143 dated Feb. 5, 2015.
International Search Report issued in Intl. Appln. No. PCT/US2014/066143 dated Mar. 31, 2015.
Written Opinion issued in Intl. Appln. No. PCT/US2014/066143 dated Mar. 31, 2015.
Office Action issued in copending U.S. Appl. No. 13/596,774 dated Apr. 15, 2015.
Amendment filed in copending U.S. Appl. No. 13/596,774 dated Jun. 30, 2015.
Office Action issued in copending U.S. Appl. No. 13/596,774 dated Jul. 27, 2015.
Amendment filed in copending U.S. Appl. No. 13/596,774 dated Oct. 19, 2015.
Notice of Allowance issued in copending U.S. Appl. No. 13/596,774 dated Nov. 3, 2015.
Office Action issued in copending U.S. Appl. No. 15/007,594 dated Mar. 17, 2016.
Amendment filed in copending U.S. Appl. No. 15/007,594 dated Sep. 13, 2016.
Office Action issued in copending U.S. Appl. No. 15/007,594 dated Oct. 21, 2016.
Amendment filed in copending U.S. Appl. No. 15/007,594 dated Feb. 10, 2017.
Office Action issued in copending U.S. Appl. No. 15/007,594 dated Mar. 30, 2017.
Amendment filed in copending U.S. Appl. No. 15/007,594 dated Jun. 30, 2017.
Office Action issued in copending U.S. Appl. No. 15/007,594 dated Jul. 19, 2017.
Reply to Office Action filed in copending U.S. Appl. No. 15/007,594 dated Oct. 12, 2017.
Extended European Search Report issued in European Appln. No. 14906383.6 dated Oct. 23, 2017.
Office Action issued in U.S. Appl. No. 15/007,594 dated Nov. 28, 2017.
Lau et al. "A Theoretical and Experimental Analysis of Radiofrequency Ablation with a Multielectrode, Phased, Duty-Cycled System." PACE. Sep. 2010: 1089-1100. vol. 33. The Authors. Journal compilation. Wiley Periodicals, Inc.
Amendment filed in copending U.S. Appl. No. 15/007,594, filed Feb. 26, 2018.
Office Action issued in copending U.S. Appl. No. 15/007,594 dated May 4, 2018.
Communication under Rule 71(3) EPC issued in European Appln. No. 14906383.6 dated Aug. 2, 2018.
Response to Office Action filed in copending U.S. Appl. No. 15/007,594 dated Aug. 28, 2018.
Office Action issued in copending U.S. Appl. No. 15/007,594 dated Oct. 10, 2018.
Extended European Search Report issued in copending European Appln. No. 18212836.3 dated Mar. 22, 2019.
Amendment filed in copending U.S. Appl. No. 15/007,594 dated Jan. 9, 2019.
Communication under Rule 71(3) EPC issued in European Appln. No. 18212836.3 dated Apr. 20, 2020.
Notice of Allowance issued in copending U.S. Appl. No. 15/581,364 dated Jul. 29, 2019.

(56) References Cited

OTHER PUBLICATIONS

Copending U.S. Appl. No. 17/027,797, filed Sep. 22, 2020.
Notice of Allowance issued in copending U.S. Appl. No. 15/007,594 dated Apr. 24, 2019.
Preliminary Amendment filed in copending U.S. Appl. No. 16/380,325 dated May 3, 2019.
Preliminary Amendment filed in copending U.S. Appl. No. 16/380,325 dated Sep. 30, 2019.
Notice of Allowance issued in copending U.S. Appl. No. 16/380,325 dated Oct. 5, 2020.
Notice of Allowance issued in copending U.S. Appl. No. 16/587,480 dated Nov. 15, 2021.
Notice of Allowance issued in copending U.S. Appl. No. 17/027,797 dated Nov. 8, 2022.

* cited by examiner

INTRA-CARDIAC MAPPING AND ABLATING

CROSS-REFERENCE TO RELATED APPLICATIONS

This application is a division of U.S. patent application Ser. No. 16/380,325, filed Apr. 10, 2019, now U.S. Pat. No. 10,918,438, issued Feb. 16, 2021, which is a continuation of prior U.S. patent application Ser. No. 15/007,594, filed Jan. 27, 2016, now U.S. Pat. No. 10,350,003, issued Jul. 16, 2019, which is a divisional of prior U.S. patent application Ser. No. 13/596,774, filed Aug. 28, 2012, now U.S. Pat. No. 9,277,960, issued Mar. 8, 2016, which claims the benefit of U.S. Provisional Patent Application No. 61/532,423, filed Sep. 8, 2011. The entire disclosure of the applications cited in this paragraph is hereby incorporated herein by reference.

BACKGROUND

Technical Field

This disclosure is generally related to surgery, and more particularly to percutaneously deployed medical devices suitable for determining locations of cardiac features or ablating regions of cardiac tissue, or both.

Description of the Related Art

Cardiac surgery was initially undertaken using highly invasive open procedures. A sternotomy, which is a type of incision in the center of the chest that separates the sternum, was typically employed to allow access to the heart. In the past several decades, more and more cardiac operations are performed using percutaneous techniques, where access to inner organs or other tissue is gained via a catheter.

Percutaneous surgeries benefit patients by reducing surgery risk, complications and recovery time. However, the use of percutaneous technologies also raises some particular challenges. Medical devices used in percutaneous surgery need to be deployed via catheter systems, which significantly increase the complexity of the device structure. As well, doctors do not have direct visual contact with the medical devices once they are positioned within the body. Positioning these devices correctly and operating the devices successfully can often be very challenging.

One example of where percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-maze procedure." During this procedure, physicians create lesions in a specific pattern in the left and right atria that block various paths taken by the spurious electrical signals. Such lesions were originally created using incisions, but are now typically created by ablating the tissue with radio-frequency (RF) energy, microwave energy, laser energy or cryogenic techniques. The procedure is performed with a high success rate under the direct vision that is provided m open procedures, but is relatively complex to perform percutaneously because of the difficulty in creating the lesions in the correct locations. Various problems, potentially leading to severe adverse results, may occur if the lesions are placed incorrectly.

Key factors which are needed to dramatically improve the percutaneous treatment of atrial fibrillation are enhanced methods for deployment, positioning, and operation of a treatment device. It is particularly important to know the position of the elements which will be creating the lesions relative to cardiac features such as the pulmonary veins and mitral valve. The continuity and transmurality characteristics of the lesion patterns that are formed can impact the ability to block paths taken within the heart by spurious electrical signals.

Several methods have been previously developed for positioning percutaneously deployed medical devices within the heart. For example, commonly assigned U.S. Patent Application Publication No. 2008-0004534 A1, which is herein incorporated by reference in its entirety, describes various intra-cardiac mapping systems based on detecting the ports through which blood flows in or out of a heart chamber. Commonly assigned U.S. Patent Application Publication No. 2009/0131930 A1, which is herein incorporated by reference in its entirety, describes a device that is percutaneously guided to a cavity of a bodily organ (e.g., a heart). The device can discriminate between fluid within the cavity (e.g., blood) and tissue dial forms an inner or interior surface of the cavity (e.g., surface tissue) to provide information or mapping indicative of a position, orientation, or both position and orientation of the device in the cavity. Discrimination may be based on flow or some other characteristic, for example electrical permittivity or force. The device can selectively ablate portions of the surface tissue based at least on the information or the mapping. In some cases, the device may detect characteristics (e.g., electrical potentials) indicative of whether ablation was successful. The device includes a plurality of transducer elements that are intravascularly or percutaneously guided in an unexpanded configuration and positioned proximate the surface tissue in an expanded configuration. Various expansion mechanisms that include helical member(s) or inflatable member(s) are described. Other forms of expansion mechanisms are described in commonly assigned U.S. Provisional Patent Application No. 61/435,213; U.S. Provisional Patent Application No. 61/485,987; U.S. Provisional Patent Application No. 61/488,639; and U.S. Provisional Patent Application No. 61/515,141 which are each herein incorporated by reference in their entirety.

Atrial fibrillation is but one example of a cardiac surgery that requires effective mapping systems that are percutaneously deliverable to various intra-cardiac cavities. The mapping systems should allow for the improved determination of the relative position of anatomical features within the intra-cardiac cavity such as pulmonary veins and mitral valve with respect to a portion of the system that is percutaneously delivered.

BRIEF SUMMARY

The present design of a medical device with enhanced capabilities for deployment, positioning and ablating within a bodily cavity such as a heart is disclosed. In particular, the device is configurable from a first or unexpanded configuration in which a portion of the device is sized for delivery to a bodily cavity via a catheter to a second or expanded configuration in which the portion of the device is expanded to position various transducer elements proximate a tissue surface within the bodily cavity. The device employs a method for distinguishing tissue from blood and may be used to deliver superior positional information of the device relative to ports in the atrium, such as the pulmonary veins and mitral valve. The device employs a method for distinguishing tissue from blood and may be used to deliver superior positional information of various anatomical features within the bodily cavity. The device may employ characteristics such as blood flow detection. The device may also improve ablation positioning and performance by using the same elements for discriminating between blood and tissue as are used for ablation. Other advantages will become apparent from the teaching herein to those of skill in the art.

A medical system may be summarized as including a structure and a plurality of transducer elements curried by the structure, the structure and the plurality of transducer elements sized to be received within an intra-cardiac cavity, the intra-cardiac cavity defined at least in part by a tissue wall with an interior surface of the tissue wall is interrupted by one or more ports positioned in fluid communication with the intra-cardiac cavity. Each transducer element of at least some of the plurality of transducer elements is responsive to blood flow to provide a respective first signal set, each respective first signal set responsive to blood flow at least proximate a respective one of the at least some of the plurality of transducer elements. The medical system includes a signal source providing a second signal set, a respective at least one signal within the second signal set provided to each of the at least some of the plurality of transducer elements. The medical system includes a controller communicatively coupled to the transducer elements and that determines information that specifies a location of each of one or more regions of the interior surface of the tissue wall and a location of each of at least one of the one or more ports on the interior surface of the tissue wall with respect to the one or more regions based at least in part on a phase of a respective first signal derived at least in part from each respective first signal set, the phase of each respective derived first signal determined relative to a phase of a respective second signal within the second signal set provided by the signal source.

The second signal set provided by the signal source may consist of a single signal. The second signal set may include a plurality of signals, each of the plurality of signals having a predetermined phase relative to a phase of another of the plurality of the signals. The phase of each respective derived first signal may be determined relative to a phase of a same or corresponding signal within the second signal set provided by the signal source. The phase of each respective derived first signal may be determined relative to a phase of a single signal within the second signal set provided by the signal source. The second signal set may include a plurality of signals, and the phases of each of at least two of the second signals within the second signal set provided by the signal source may differ from one another by a predetermined amount. Each respective second signal within the second signal set provided by the signal source may have a predetermined phase relative to a phase of the respective at least one signal within the second signal set provided to the respective transducer element of the at least some of the plurality of transducer elements associated with the respective derived first signal whose phase is determined relative to the phase of the respective second signal.

The medical system may further include at least one synchronous demodulator that provides the phase of each respective derived first signal relative to the phase of the respective second signal within the second signal set provided by the signal source. The controller may perform a frequency domain transform to determine the phase of each respective derived first signal relative to the phase of the respective second signal within the second signal set provided by the signal source. The controller may perform a Fourier transform to determine the phase of each respective derived first signal relative to the phase of the respective second signal within the second signal set provided by the signal source. Each respective second signal may include a number of alternating HIGH periods and LOW periods within a predetermined time duration, one pair of adjacent or consecutive HIGH and LOW periods defining a respective duty cycle. Each of the HIGH periods may have a duration substantially equal to a duration of a respective one of the LOW periods and may repeat with a frequency less than 2.5 Hertz. Each of the HIGH periods may be substantially equal to a respective one of the LOW periods and may repeat with a frequency equal to or less than 1 Hertz. Each respective at least one signal within the second signal set provided to each of the at least some of the plurality of transducer elements may include a number of alternating HIGH periods and LOW periods within a predetermined time duration, one pair of adjacent HIGH and LOW periods defining a respective duty cycle. Each of at least one of the HIGH periods and the LOW periods may include a plurality of periodic continuous signals. Each first signal set may vary based at least on convective heat transfer changes proximate a respective one of the at least some of the plurality of transducer elements. Each transducer element of the at least some of the plurality of transducer elements may include at least one resistive member, each at least one resistive member arranged to receive the respective at least one signal of the second signal set to vary temperature of the transducer element of the at least some of the plurality of transducer elements. Each signal in each respective first signal set may include a number of alternating HIGH periods and LOW periods within a predetermined time duration, one pair of adjacent HIGH and LOW periods defining a respective duty cycle. The structure may be selectively configurable between a delivery configuration in which the structure is percutaneously deliverable to the intra-cardiac cavity and an expanded configuration in which the structure is expanded within the intra-cardiac cavity, the structure sized too large to be delivered percutaneously to the intra-cardiac cavity in the expanded configuration. At least a first transducer element of the at least some of the plurality of transducer elements may be spaced on the structure from a second transducer element of the at least some of the plurality of transducer elements such that at least the first transducer element of the at least some of the plurality of transducer elements is positioned on a portion of the structure lying across a portion of one of the one or more ports and the second transducer element of the at least some of the plurality of transducer elements is positioned on a portion of the structure which does not overlie the one of the one or more ports when the structure is in the expanded configuration.

The medical system may further include an ablation source coupled to transfer energy between the ablation source and at least one of the transducer elements.

The medical system may further include a radio-frequency generator coupled to provide a varying current to at least one transducer element of the plurality of transducer elements to provide energy to the tissue wall from the at least one transducer element. The controller may provide the information in the form of a map of the location of at least one of the one or more regions of the interior surface of the tissue wall and the location of the at least one of the one or more ports relative to the location of the at least one of the one or more regions of the interior surface of the tissue wall. The controller may provide a visual representation of the phase of each respective derived first signal.

A medical system may be summarized as including a structure, one or more transducer elements carried by the structure, the structure and the one or more transducer elements sized to be received within an intra-cardiac cavity, the intra-cardiac cavity defined at least in part by a tissue wall with an interior surface of the tissue wall interrupted by one or more ports positioned in fluid communication with the intra-cardiac cavity. The medical system includes a signal source providing a respective input signal to each of the one or more transducer elements. The medical system includes a sensing system sensing temperature change at least proximate to each of the one or more transducer elements, the sensing system providing a respective set of one or more response signals for each of the one or more transducer elements, each set of one or more response signals responsive to the temperature change at least proximate to a respective one of the one or more transducer elements. The medical system includes a controller that derives at least one signal from each set of one or more response signals and determines a respective set of one or more values representative of a phase difference between each derived at least one signal and the respective input signal provided to the transducer element of the one or more transducer elements associated with the set of one or more response signals. The controller determines information specifying a location of each of one or more regions of the interior surface of the tissue wall and a location of each of at least one of the one or more ports on the interior surface of the tissue wall with respect to the one or more regions based at least on each determined respective set of one or more values.

The signal source may provide a same or corresponding input signal to each of the one or more transducer elements. The signal source may provide a single input signal to each of the one or more transducer elements. The one or more transducer elements may include a plurality of transducer elements, and each respective input signal provided by the signal source to each transducer element of the plurality of transducer elements may have a predetermined phase relative to the respective input signal provided to another transducer element of the plurality of transducer elements. The one or more transducer elements may include a plurality of transducer elements, and each respective input signal provided by the signal source to each transducer element of the plurality of transducer elements may have a different frequency than a frequency of the respective input signal provided to another transducer element of the plurality of transducer elements.

The medical system may further include a synchronous demodulator communicatively coupled between the controller and at least one of the transducer elements to provide the phase of each derived at least one signal relative to a phase of a respective signal provided by the signal source. The controller may perform a frequency domain transform to determine each respective set of one or more values. The controller may perform a Fourier transform to determine each respective set of one or more values. Each respective input signal may include a number of alternating HIGH periods and LOW periods within a predetermined time duration, one pair of adjacent HIGH and LOW periods defining a respective duty cycle. Each of at least one of the HIGH periods and the LOW periods of each respective input signal may include a plurality of periodic continuous signals. Each set of one or more response signals may include a voltage signal and an electrical current signal.

The medical system may further include an analog-to-digital convener arranged to sample each of the voltage signal and the electrical current signal in each set of one or more response signals synchronously with the alternating HIGH periods and LOW periods of the respective input signal corresponding to the set of one or more response signals. Each set of one or more response signals may include a voltage signal and an electrical current signal. The sensing system may include one or more resistance temperature detectors, the temperature change at least proximate to each of the one or more transducer elements sensed by a respective one of the one or more resistance temperature detectors. The structure may be selectively configurable between a delivery configuration in which the structure is percutaneously deliverable to the intra-cardiac cavity and an expanded configuration in which the structure is expanded within the intra-cardiac cavity, the structure sized too large to be delivered percutaneously to the intra-cardiac cavity in the expanded configuration. The one or more transducer elements may include a plurality of transducer elements, at least a first transducer element of the plurality of transducer elements spaced on the structure from a second transducer element of the plurality of transducer elements such that at least the first transducer element of the plurality of transducer elements is positioned on a portion of the structure lying across a portion of one of the one or more ports and the second transducer element of the plurality of transducer elements is positioned on a portion of the structure which docs not overlie the one of the one or more ports.

The medical system may further include an ablution source coupled to transfer energy to one or more transducer elements.

The medical system may further include a radio-frequency generator arranged to provide a varying current to at least one transducer element of the plurality of transducer elements to provide energy to the tissue wall from the at least one transducer element of the plurality of transducer elements. The controller may provide the information in the form of a map of the location of at least one of the one or more regions of the interior surface of the tissue wall and the location of the at least one of the one or more ports relative to the location of the at least one of the one or more regions of the interior surface of the tissue wall. The controller may provide a map of each determined respective set of one or more values.

A medical system may be summarized as including a structure and a plurality of transducer elements carried by the structure, the structure and the plurality of transducer elements sized to be received within an intra-cardiac cavity of a heart, the intra-cardiac cavity defined at least in part by a tissue wall. An interior surface of the tissue wall is interrupted by one or more ports positioned in fluid communication with the intra-cardiac cavity. Each of at least some of the plurality of transducer elements is responsive to blood flow proximate at least proximate thereto. The medical system includes a controller communicatively coupled to the transducer elements and which determines information that specifics a location of each of one or more regions of the interior surface of the tissue wall and a location of each of at least one of the one or more ports on the interior surface of the tissue wall with respect to the one or more regions based at least in part on a phase of a blood flow signal indicative of the blood flow at least proximate at least one of the transducer elements relative to a phase of a drive signal supplied to the respective one of the transducer elements.

Various medical systems may include combinations and subsets of those summarized above.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIG. 10F is a graph or plot of a Fourier power series phase versus time for the first resistive member under "Flow" and "No Flow" conditions for a 2-volt input voltage signal.

DETAILED DESCRIPTION

Figure 1:
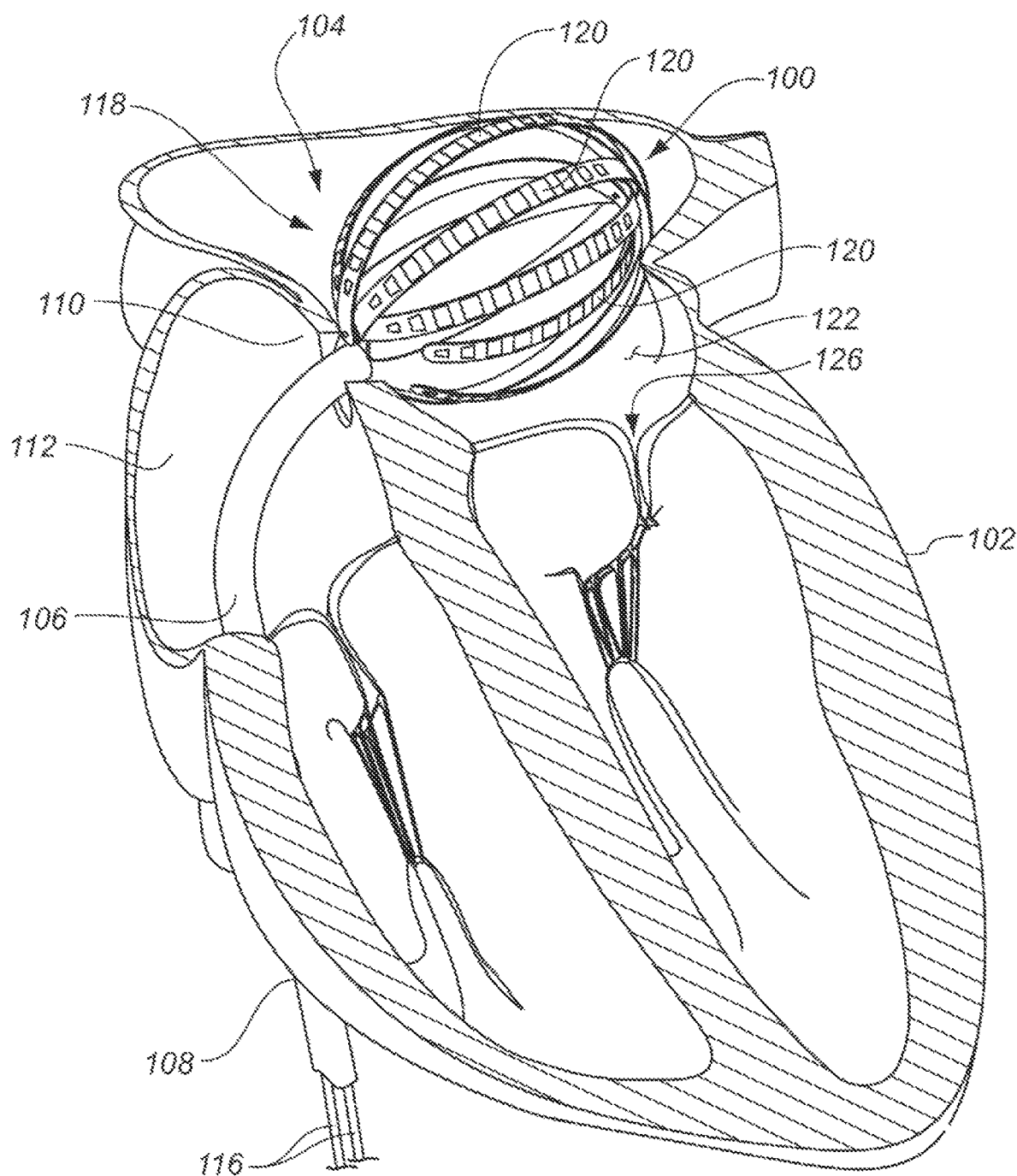
FIG. 1 is a cutaway diagram of a heart showing a medical device according to one illustrated embodiment percutaneously placed in a left atrium of the heart.

In the following description, certain specific details are set forth in order to provide a thorough understanding of various embodiments of the invention. However, one skilled in the an will understand that the invention may be practiced without these details. In other instances, well-known structures associated with radio-frequency (RF) ablation and electronic controls such as multiplexers have not been shown or described in detail to avoid unnecessarily obscuring descriptions of the embodiments of the invention.

The word "ablation" should be understood to mean any disruption to certain properties of the tissue. Most commonly, the disruption is to the electrical conductivity and is achieved by heating, which can be generated with resistive or of radio-frequency (RF) techniques for example. Other properties, such as mechanical, or chemical and other means of disruption, such as optical, are included when the term "ablation" is used.

The word "fluid" should be understood to mean any fluid that can be contained within a bodily cavity or can flow into and/or out of a bodily cavity via one or more bodily openings positioned in fluid communication with the bodily cavity. In the ease of cardiac applications, fluid such as blood flows into and out of various intra-cardiac cavities (e.g., the left atrium and the right atrium).

The word "bodily opening" should be understood to be a naturally occurring bodily opening or channel; a bodily opening or channel formed by an instrument or tool using techniques that can include, but are not limited to, mechanical, thermal, electrical, chemical, and exposure or illumination techniques; a bodily opening or channel formed by trauma to a body; or various combinations of one or more of the above. A bodily opening can include additional dements having respective openings or channels and positioned within the bodily opening (e.g., a catheter sheath).

The word "tissue" should be understood to mean any tissue that is used to form a surface within a bodily cavity, a surface of feature within a bodily cavity, or a surface of a feature associated with a bodily opening positioned in fluid communication with the bodily cavity. The tissue can include part or all of a tissue wall or membrane that includes a surface that defines a surface of the bodily cavity. In this regard, the tissue can form an interior surface of the cavity that surrounds a fluid within the cavity. In the ease of cardiac applications, tissue can include tissue used to form an interior surface of an intra-cardiac cavity such as a left atrium or right atrium.

The term "transducer element" (or "element" in some embodiments) in this disclosure should be interpreted broadly as any component capable of distinguishing between fluid and tissue, sensing temperature, creating heat, providing energy (e.g., radio-frequency (RF)) energy, ablating tissue and measuring electrical activity of a tissue surface, or any combination thereof. A transducer element can convert input energy of one form into output energy of another form. Without limitation, a transducer element can include an electrode operable to apply an electrical signal to tissue or an electrode operable to generate an electrical signal in response to a physical or electrical characteristic of tissue. Transducer elements may take the form of some other transducer device, for example a transducer operable to apply energy to, or remove energy from, tissue. Alternatively, or additionally, a transducer element may take the form of some other transducer device, for example a transducer operable to sense a physical or other characteristic of tissue. A transducer dement may be constructed from several parts, which may be discrete components or may be integrally formed.

Reference throughout this specification to "one embodiment" or "an embodiment" or "an example embodiment" means that a particular feature, structure or characteristic described in connection with the embodiment is included in at least one embodiment of the present invention. Thus, the appearances of the phrases "in one embodiment" or "in an embodiment" and the like in various places throughout this disclosure are not necessarily all referring to the same embodiment. Furthermore, the particular features, structures, or characteristics may be combined in any suitable manner in one or more embodiments.

Various embodiments of percutaneously or intravascularly deployed medical devices are described herein. Many of the described devices are moveable between an unexpanded configuration in which a portion of the device is sized for passage though a bodily opening leading to cavity within a body, and an expanded configuration in which the portion of the device expands within the bodily cavity. In some example embodiments, the device senses characteristics (e.g., convective cooling) that distinguish between fluid (e.g., blood) and tissue forming an interior surface of the bodily cavity. Such sensed characteristics allow a medical system to map the cavity, for example using positions of openings or ports into and out of the cavity to determine a position or orientation (i.e., pose), or both position and orientation of the portion of the device in the bodily cavity. In some example embodiments, the devices are capable of ablating tissue in a desired pattern within the bodily cavity. In some example embodiments, the devices are capable of sensing characteristics (e.g., electrical activity) indicative of whether an ablation has been successful.

An example of a mapping performed by devices according to various embodiments is to locate the position of various bodily openings leading to the pulmonary veins as well as the mitral valve on the interior surface of the left atrium. In some example embodiments, the mapping is based at least on locating such bodily openings by differentiating between fluid and tissue. There are many ways to differentiate tissue from a fluid such ax blood or to differentiate tissue from a bodily opening. One approach to determining the locations is to use the convective cooling of healed transducer elements by the blood. For example, a slightly heated mesh of transducer elements that is positioned adjacent to the tissue that forms the interior surface(s) of the atrium and across the ports of the atrium will be cooler at the areas which are spanning the pons carrying blood flow.

FIG. 1 shows a device 100 of a medical system useful in diagnosing or treating a bodily organ, for example a heart 102, according to one illustrated embodiment.

Device 100 can be percutaneously or intravascularly inserted into a portion of the heart 102, such as an intra-cardiac cavity like left atrium 104. In this example, the device 100 is delivered via a catheter 106 inserted via inferior vena cava 108 and penetrating through a bodily opening in transatrial septum 110 from right atrium 112. In other embodiments, other paths may be taken.

Catheter 106 is an elongated flexible rod member appropriately sized to be delivered percutaneously or intravascularly. Catheter 106 may include one or more lumens (not shown). The lumen(s) may carry one or more communications and/or power paths, for example one or more electrical conductors 116. Electrical conductors 116 provide electrical connections to device 100 that are accessible externally from a patient in which device 100 is inserted.

As discussed in more detail herein, device 100 includes a structure or frame 118 which assumes a delivery or unexpanded configuration for delivery to left atrium 104. Frame 118 is expanded (i.e., shown in a deployed or expanded configuration in FIG. 1) upon delivery to left atrium 104 to position a plurality of transducer elements 120 (only three called out in FIG. 1) proximate the interior surface formed by tissue 122 of left atrium 104. In this example embodiment, at least some of the transducer elements 120 are used to sense a physical characteristic of a fluid (e.g., blood) or tissue 122, or both fluid and tissue 122 that may be used to determine a position, orientation (i.e., pose), or both position and orientation of a portion of device 100 in left atrium 104. For example, transducer elements 120 may be used to determine a location of pulmonary vein ostiums (not shown), a mitral valve 126, or both. In this example embodiment, at least some of the transducer elements 120 may be used to selectively ablate portions of the tissue 122. For example, some of the elements may be used to ablate a pattern around the bodily openings, ports or pulmonary vein ostiums, for instance to reduce or eliminate the occurrence of atrial fibrillation.

Figure 2:
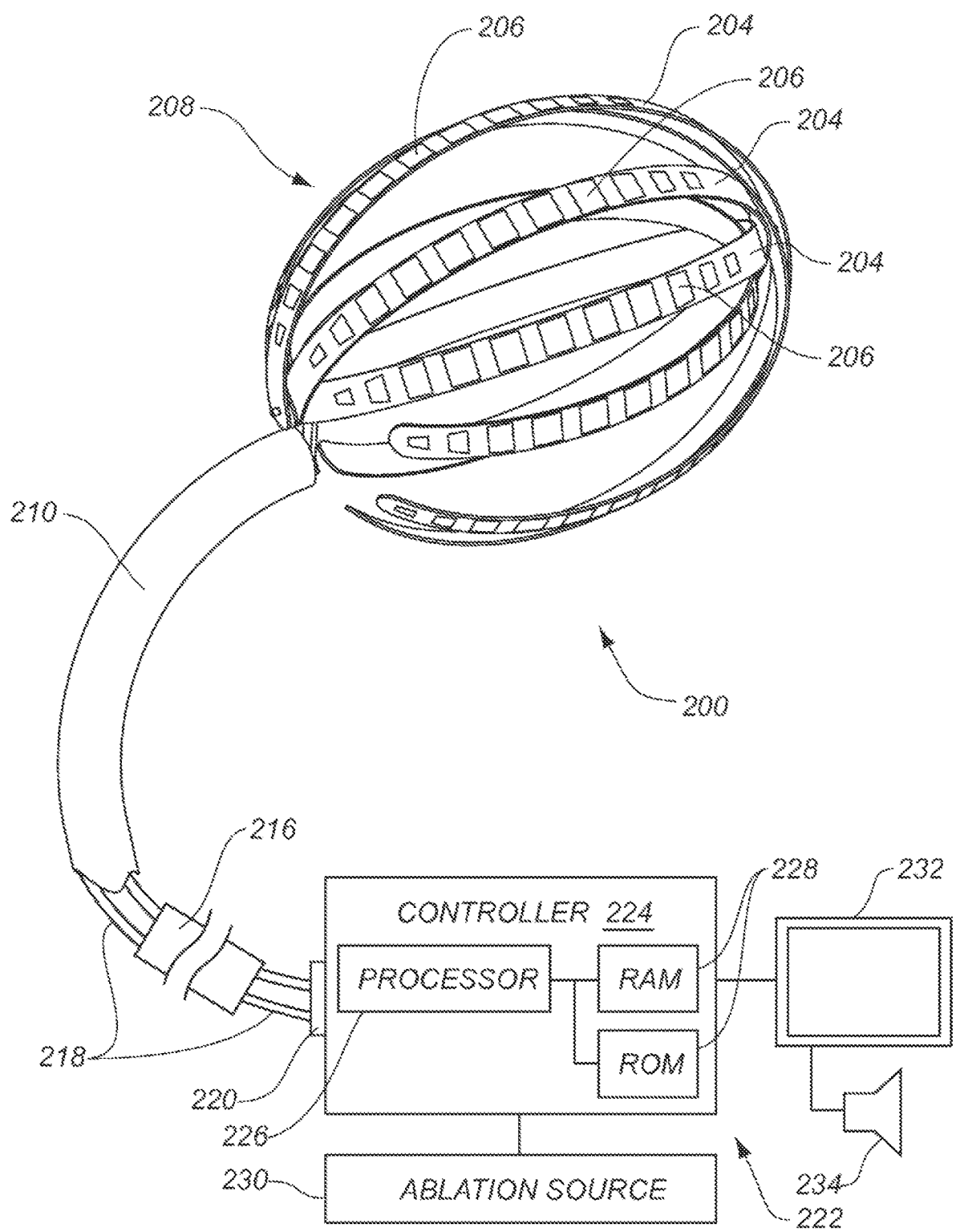
FIG. 2 is a partial schematic diagram of a medical system according to one illustrated embodiment, including a control system, a display, and a medical device having an expandable frame and an assembly of elements.

FIG. 2 schematically shows a device 200 according to one illustrated embodiment. Device 200 includes a plurality of flexible strips 204 (three called out in FIG. 2) and a plurality of transducer elements 206 (three called out in FIG. 2) arranged to form a two- or three-dimensional grid or array capable of mapping an inside surface of a bodily cavity or lumen without requiring mechanical scanning. The flexible strips 204 are arranged in a framed structure 208 that is selectively movable between an unexpanded configuration and an expanded configuration that may be used to force flexible strips 204 against a tissue surface within the bodily cavity or position the flexible strips in the vicinity of the tissue surface. The flexible strips 204 can form part of a flexible circuit (also known as a flexible printed circuit board (PCB) circuit). The flexible strips 204 can include a plurality of different material layers. The expandable frame 208 can include one or more resilient members. Expandable frame 208 can include one or more elongate members. Each of the one or more elongate members can include a plurality of different material layers. Expandable frame 208 can include a shape-memory material, for instance Nitinol. Expandable frame 208 can include a metallic or non-metallic material by way of non-limiting example. The incorporation of a specific material into expandable frame 208 may be motivated by various factors including the specific requirements of each of the unexpanded configuration and expanded configuration, the required position, orientation (i.e., pose), or both position and orientation of expandable frame 208 in the bodily cavity and the requirements for successful ablation of a desired pattern.

Expandable frame 208, as well as flexible strips 204, can be delivered and retrieved via a catheter member, for example a catheter sheath introducer 210. Flexible strips 204 may include one or more material layers. Flexible strips 204 may be made of one or more thin layers of Kapton® (polyimide), for instance 0.1 mm thick. Transducer elements (e.g., electrodes and/or sensors) 206 may be built on the flexible strips 204 using conventional printed circuit board processes. An overlay of a thin electrical insulation layer (e.g., Kapton® about 10-20 micron thick) may be used to provide electrical insulation, except in areas needing electrical contact to blood and tissue. In some embodiments, flexible strips 204 can form a portion of an elongated cable 216 of control leads 218, for example by stacking multiple layers, and terminating at a connector 220. In some example embodiments, flexible strips 204 are formed from flexible substrates onto which electrically conductive elements (e.g., conductive lines or traces) are provided. In some example embodiments flexible strips 204 form flexible circuit structures. In some example embodiments, a portion of device 200 is typically disposable.

Device 200 can communicate with, receive power from or be controlled by a control system 222 of the medical system. The control system 222 can include a controller 224 having one or more processors 226 and one or more non-transitory storage media 228 that store instructions that are executable by the processors 226 to (a) process information received from device 200, (b) control operation of device 200 (e.g., activating selected transducer elements 206 to ablate tissue, or both (a) and (b). Controller 224 can include one or more controllers. Control system 222 may include an ablation source 230. The ablation source 230 may, for example, provide electrical current or power, light or low temperature fluid to the selected transducer elements 206 to cause ablation. The ablation source can include an electrical current source or an electrical power source. Control system 222 can also include one or more user interface or input/output (I/O) devices, for example one or more displays 232, speakers 234, keyboards, mice, joysticks, track pads, touch screens or other transducers to transfer information to or from a user, for example a care provider such as a physician or technician. For example, output from the mapping process may be displayed on a display 232.

While the embodiments disclosed above are described with examples of cardiac mapping, the same or similar embodiments may be used for mapping other bodily organs, for example gastric mapping, bladder mapping, arterial mapping and mapping of any lumen or cavity into which the devices of the present invention may be introduced.

Figure 3:
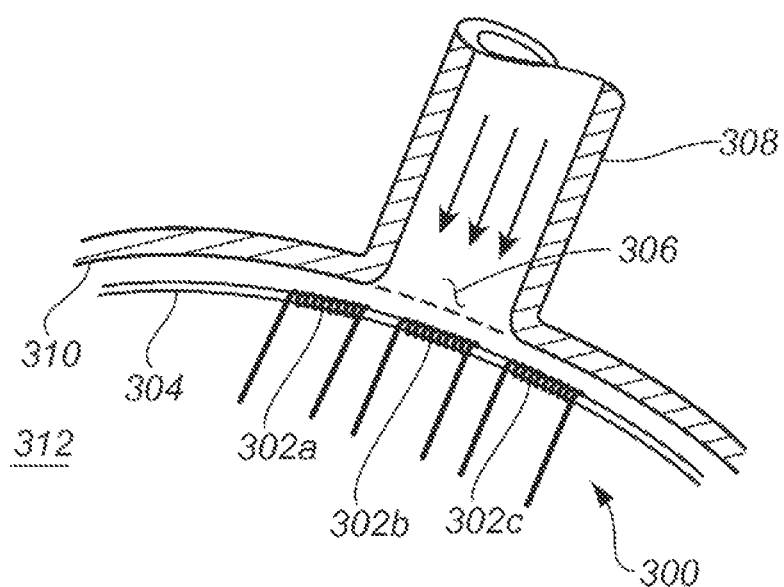
FIG. 3 is a cutaway diagram of a portion of an atrium and a number of elements showing how the elements can sense convective cooling to locate a position of ports.

FIG. 3 shows a portion of a medical device 300, according to one illustrated embodiment.

The portion of the device 300 is particularly suitable to sense convective cooling. Device 300 includes transducer elements 302a, 302b, 302c (collectively 302) capable of producing heat. Transducer elements 302 can, for example, be made of insulated resistive wire, such as Nickel, or Nickel-Iron composition. The resistive wire may be mounted on an expandable frame 304. In this embodiment, the expandable frame 304 can also be made of a material that has high impedance. Current passed through each transducer element 302 raises the temperature of the transducer element 302 by a nominal amount. A rise of 0.5-3.0 degrees Celsius above normal blood temperature has been found to be sufficient in most cases. The power required to raise the temperature in this particular embodiment is about 10-50 mW per transducer element 302. In this illustrated embodiment which reflects a cardiac application, a central one of the transducer elements 302b, which is placed across port 306 of an ostium of pulmonary vein 308 will be cooled by blood flow more than the neighboring transducer elements 302a, 302c which are adjacent to the inner or interior surface provided by tissue 310 that surrounds an intra-cardiac cavity (e.g., atrium 312). Transducer elements 302 which are found to be cooler on expandable frame 304 indicate the locations of pons 306 in the tissue 310 that provides the atrium interior surface. This example embodiment need not require intimate contact with tissue 310, since even at a distance of a few millimeters from the ports 306 the cooling effect is significant compared to the cooling effect at a similar distance from the tissue 310 of the heart wall. A backside (i.e., the side facing away from ports 306 or tissue 310) of the transducer elements 302 may be thermally insulated for improved performance of both sensing and ablation. In this regard, the use of flat elongated members in the expandable frame 304 may be advantageous. A cross-section of such a flat elongated member may, for example have dimensions of 0.2 mm×2 mm for stainless steel or 0.3 mm×2.5 mm for Nitinol. The insulation on the back side of the transducer elements 302 may take the form of a coat of silicone rubber. It is understood that other suitable materials or other suitable dimensions can be employed in other example embodiments. In some embodiments, the elongate members may have varying cross-sectional dimensions as the respective lengths of the elongate members are traversed.

If the transducer elements 302 are made of a material that undergoes a significant change in resistance with temperature, the temperature drop can be determined from the resistance of the transducer element 302. The resistance can be determined by measuring the voltage across the transducer element 302 for a given current, or alternatively, by measuring the current through the transducer element 302 for a given voltage, for example via a Wheatstone bridge circuit. Some example embodiments may take advantage of convective cooling by the flow of blood, and at least some of the transducer elements 302 function as a hot wire anemometer. Nickel wire is an example of a suitable material to use, as nickel is inert, highly resistive and has a significant temperature coefficient of resistance (about 0.6% per deg. Celsius). Since the resistance of the transducer elements 302 can be made to be relatively low (i.e., typically less than 5 ohm), electrical noise can be reduced and temperature changes as low as 0.1-1 deg. Celsius can be detected. Several techniques can be employed to improve this sensitivity. One technique involves sampling the voltage waveform in synchronization with the heart rate. Another technique involves removing the average voltage via AC coupling and only amplifying the voltage change or derivative. Yet another technique involves passing the signal through a digital band puss filter having a center frequency tracking the cardiac cycle, the pulmonary cycle, or both the cardiac and the pulmonary cycles.

FIGS. 4A-4H show various transducer element configurations according to various embodiments. Each of the embodiments of FIGS. 4A-4F shows transducer elements which have been constructed using microelectronic circuit substrates, materials and techniques. Each of the embodiments of FIGS. 4A-4F shows transducer elements which have been constructed into flexible printed circuit boards (also known as flexible circuit structures). Flexible circuit structures typically include a flexible substrate layer that includes a dielectric material (e.g., polyester, LCP, polyimide) and an electrically conductive layer that includes various electrically conductive materials (e.g., gold or copper). An electrically conductive interconnection circuitry may be provided by various ones of the electrically conductive layers by various techniques including sputtering, plating and etching. One or more material layers (e.g., adhesion layers, insulation layers) may be additionally provided in the flexible circuit structures.

The transducer elements may be affixed to a frame similar to the expandable frame 208 shown in FIG. 2, which may be made from a material such as Nitinol by way of non-limiting example. In some embodiments, each flexible circuit structure includes a plurality of substrates or plurality of material layers, at least one of the substrates or material layers forming pan of an expandable frame. In some example embodiments, the flexible substrates may be of such a thickness that the flexible substrates can form the expandable frame. A flexible substrate made of polyimide having a thickness, for instance, of approximately 0.01-0.3 mm may be suitable in some applications. In some applications, the transducer elements can also be constructed using discrete components. The embodiments illustrated in FIGS. 4G-4H do not employ flexible circuits.

Figure 4A:
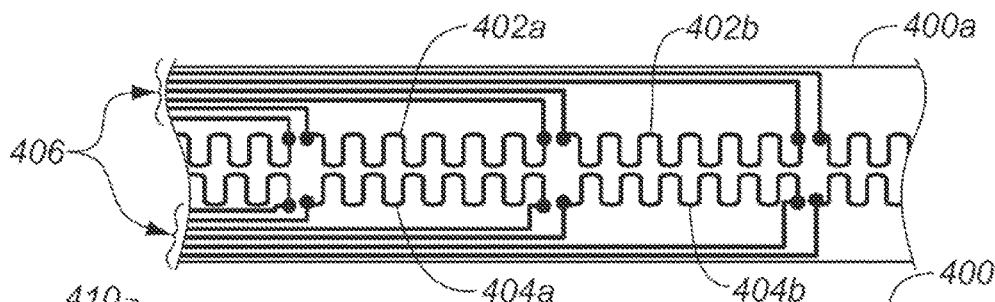
FIG. 4A is a top plan view of element construction for flow sensing.

FIG. 4A shows a flexible circuit substrate 400a that carries a combination of transducer elements, in particular sensor transducer elements 402a, 402b (collectively 402, only two called out in FIG. 4A) which sense convective cooling and ablation transducer elements 404a, 404b (collectively 404, only two called out in FIG. 4A) which are operable to ablate tissue. Leads, collectively 406, include electrically conductive Sines or traces that extend to respective ones of the transducer elements 402, 404. The leads 406 may be coupled to a control system (e.g., control system 222 of FIG. 2), which may provide (a) communications, (b) power, (c) control, or combinations of (a), (b) and (c) with the transducer elements 402, 404.

Figure 4B:
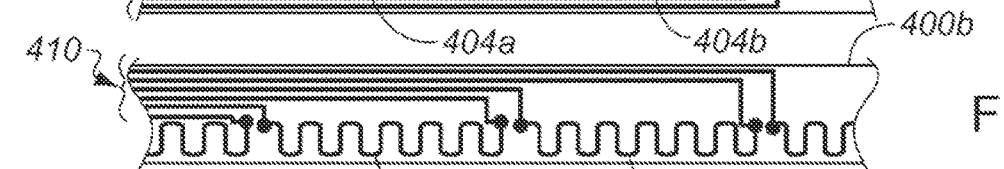
FIG. 4B is a top plan view according to yet another illustrated embodiment

FIG. 4B shows a flexible circuit substrate 400b that carries a number of combined sensor and ablation transducer elements 408a, 408b (collectively 408, only two called out in FIG. 4B) that both sense flow and ablate non-blood tissue. This example embodiment may be a significant advantage since a device with combined sensor and ablation transducer elements 408 can measure flow at the exact spot that ablation will occur, while requiring fewer components, thus improving precision and reducing size. In this embodiment, each combined sensor and ablation transducer element 408 has respective leads, collectively 410, coupled to a control system (e.g., control system 222 of FIG. 2).

A combined sensor and ablation transducer element 408 that can be used for both sensing flow and ablating can be made using standard printed circuit construction processes. For example, a 2-4 mil copper trace on a polyimide substrate can be used. Copper changes resistance sufficiently enough with temperature to be used to determine blood flow in a manner similar to that discussed above. Copper can also be used as an ablation element by applying sufficient current through the copper to cause the combined sensor and ablation transducer element 408 to heat resistively, for example to a temperature above 60° C. Power in the range of approximately 130-250 mW delivered to a copper pattern that has external dimensions of 3 mm×10 mm and is thermally insulated on the side away from the tissue may be sufficient to transmurally ablate a 3 mm deep section of the tissue that surrounds at least a portion of the cavity. In this approach, the tissue is heated by conduction from the copper combined sensor and ablation transducer element 408. When the tissue is healed by conduction, the combined sensor and ablation transducer element 408 may be electrically insulated from the tissue.

Alternatively, the combined sensor and ablation transducer element 408 can also be used to ablate tissue by using the combined sensor and ablation transducer element 408 as an electrode for delivering RF energy to the tissue. In this scenario, electrical current is transferred directly to the tissue and the tissue is resistively heated by the current flow. When RF energy is delivered, a preferred method may be to have low electrical impedance between the combined sensor and ablation transducer element 408 and the tissue. In some embodiments, an electrically conductive electrode pad (not shown) is positioned between sensor portions of transducer element 408 and the tissue. Delivering RF energy is also possible if the combined sensor and ablation transducer element 408 is capacitively coupled to the tissue, so long as the impedance at the frequency of the employed RF energy is sufficiently low (i.e., typically under a few 100 ohms or less tor a combined sensor and ablation transducer element 408 of the size mentioned above). It is noted that in the case where the combined sensor and ablation transducer element 408 has a low electrical impedance connection to the tissue for low frequencies, it is also possible to use the combined sensor and ablation transducer element 408 to sense an electrical potential in the tissue that surrounds at least a portion of the heart cavity, for example to generate an intra-cardiac electrogram. Thus, it is possible for the same combined sensor and ablation transducer element 408 to sense flow, sense electrical potential of the tissue that surrounds a portion of the heart cavity, and ablate the tissue. In some example embodiments, combined sensor and ablation transducer element 408 can also stimulate (i.e., pace) tissue.

Figure 4C:
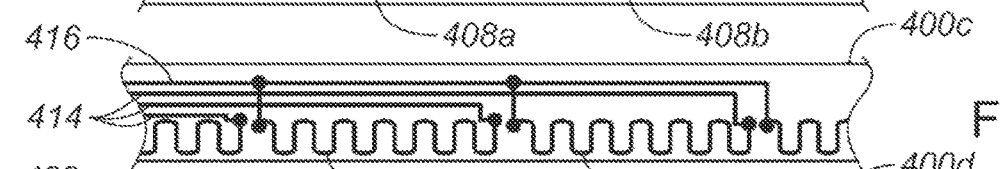
FIG. 4C is a top plan view according to yet another illustrated embodiment.

FIG. 4C shows a flexible circuit substrate 400c that carries a number of combined flow sensor, ablation and temperature transducer elements 412a, 412b (collectively 412, only two called out in FIG. 4C) that can be used to sense flow, ablate tissue that surrounds at least a portion of the heart cavity and sense or monitor temperature. The sensed or monitored temperature can be used for ablation control, by way of non-limiting example. A single control lead (three shown), collectively 414, is required per each combined flow sensor, ablation and temperature transducer element 412. A common return lead 416 is connected to the multiple combined flow sensor, ablation and temperature transducer elements 412. The combined flow sensor, ablation and temperature transducer element 412 can take the form of a low resistance resistor, for example a resistor formed by a 30-100 micron wide trace of 10-30 micron thick copper foil. Such a resistor has a typical resistance of 0.5-20 ohms and can be used as a combined flow sensor, ablation and temperature transducer element 412 to sense flow, perform ablation and sense temperature. When used as a temperature sensor, resistance changes of about 1% for a 2.5 degree Celsius temperature change are typical.

Figure 4D:
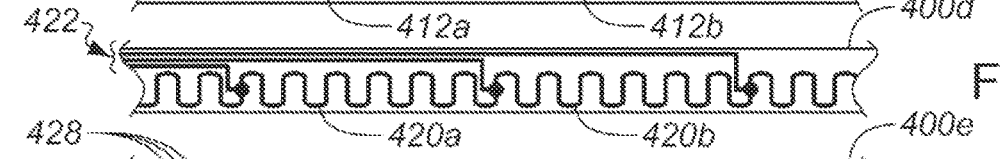
FIG. 4D is a top plan view according to yet another illustrated embodiment.

FIG. 4D shows a flexible circuit substrate 400d that carries a number of adjacent transducer elements 420a, 420b (collectively 420, only two called out in FIG. 4D). The transducer elements 420 share common control leads 422. This feature is an advantage as it dramatically reduces the number of leads 422 needed to return to the control system (e.g., control system 222 of FIG. 2).

Figure 5:
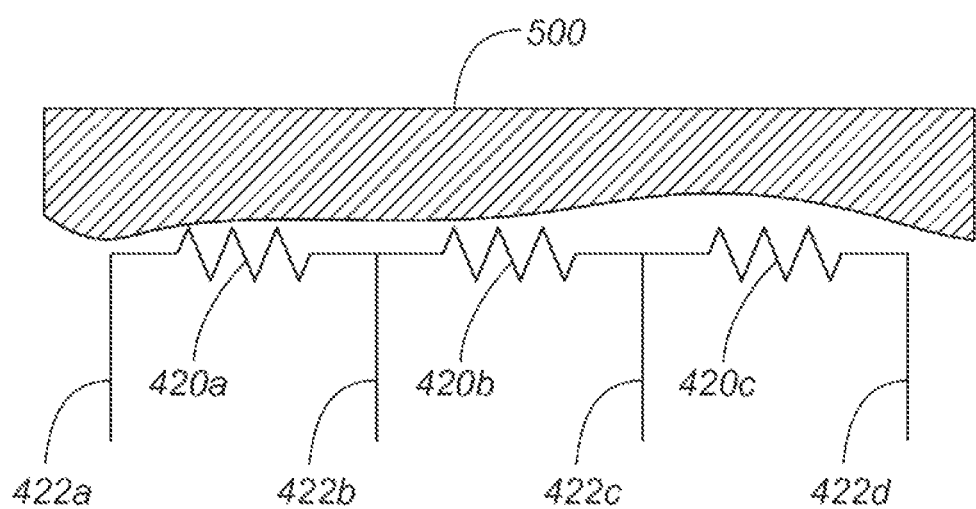
FIG. 5 is a diagram showing how common leads can be shared by elements used for flow sensing according to various example embodiments.

FIG. 5 schematically shows an expanded example of a portion of the embodiment of FIG. 4D positioned proximate tissue 500. To determine flow by measuring the resistance of transducer element 420b, the voltage at lead 422a and lead 422b should be made equal and the voltage at lead 422c and lead 422d should be made equal, but to a different voltage than that of lead 422a and lead 422b. In this condition, negligible current will flow through transducer element 420a and transducer element 420c. Therefore, the current flowing through lead 422b and lead 422c is the same as the current flowing through the transducer element 420b, and the resistance of the transducer element 420b can be calculated in a straightforward manner using the relationship V=I/R, where V is the voltage, I is the current and R is the resistance.

To cause the transducer element 420b to heat to a temperature sufficient to cause ablation, while not causing ablation at transducer element 420a and transducer element 420c:
- the voltage at lead 422c and lead 422d should be made equal;
- the voltage at lead 422b should be made higher than the voltage at lead 422c such that sufficient power is delivered to the transducer element 420b to cause the transducer element 420b to heat to the appropriate temperature; and
- the voltage at lead 422a should be set a value that is a fraction of that at lead 422b such that the power delivered to the transducer element 420a is not sufficient to cause the temperature of the transducer element 420a to rise enough for tissue ablation.

For example, if the voltages at lead 422c and lead 422d are set to 0 volts, voltage at lead 422b is set to n volts and voltage at lead 422a is set to ⅔ n volts, the power delivered to the transducer element 420a will be only 11% of that delivered to the transducer element 420b. This technique of having adjacent transducer elements 420 share common control leads 422 can, for example, be used in a elongated one-dimensional array of connected transducer elements 420 or may be applied to transducer elements 420 connected in two-dimensional or in three-dimensional arrays.

Figure 4E:
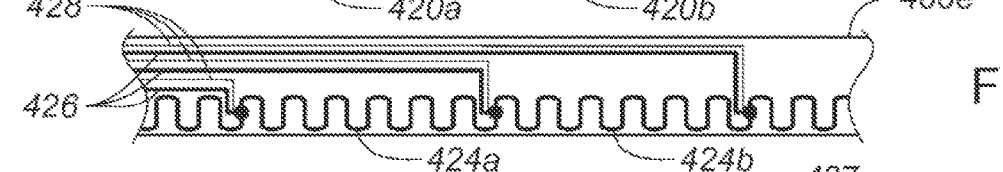
FIG. 4E is a top plan view according to yet another illustrated embodiment.

FIG. 4E shows a flexible circuit substrate 400e that carries a number of transducer elements 424a, 424b (collectively 424, only two called out in FIG. 4E). The transducer elements 424 are coupled to leads 426, similar to leads 422 of the embodiment of FIG. 4D, and to additional leads 428, which have been added to measure the voltage at the ends of the transducer elements 424. This feature advantageously increases the accuracy in determining the resistance, and thus temperature, of the transducer elements 424. The leads 426 that provide the current to the transducer elements 424 typically have a small voltage drop across them that can affect the accuracy of the resistance calculation of the transducer element 424. The additional leads 428 will have a very limited amount of current flowing through them, and thus the voltage drop through the leads 428, even for a distance of several meters will be negligible, and the voltage drop across the transducer elements 424 can be determined accurately.

Figure 4F:
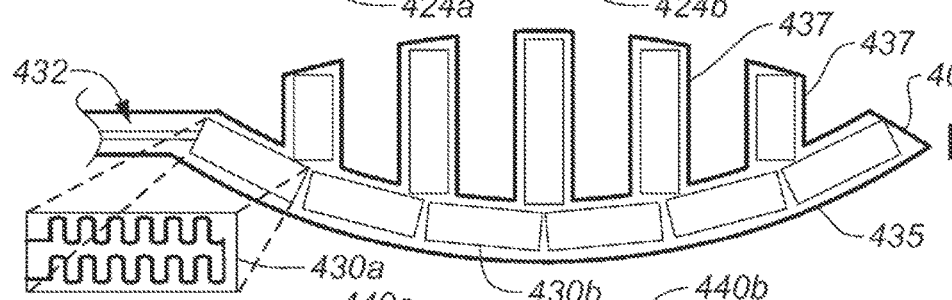
FIG. 4F is a top plan view according to yet another illustrated embodiment.

FIG. 4F shows a flexible circuit substrate 400f that includes a main branch 435 and a plurality of side branches 437 (only two called out), each of these branches carrying various transducer elements. In this illustrated embodiment, the branched flexible PCB substrate 400f is leaf shaped, although it is understood that other shapes can be employed in other example embodiments of the invention. For example, various ones of side branches 437 can be disposed on each side of main branch 435. Additionally, side branches 437 can have different sizes than those illustrated in FIG. 4F. An expandable frame (e.g., expandable frame 208 of FIG. 2) may be covered by several of the branched substrates 400f, each of which will cover or be proximate a respective portion of live tissue that forms an interior surface of the cavity of a bodily organ when in use. Each of the branched substrates caries a plurality of transducer elements 430a, 430b (collectively 430, only two called out in FIG. 4F). In this example, the transducer elements 430 are coupled together as described above in the embodiment of FIG. 4D. Leads 432 (only one set shown) electrically connect each transducer element 430 to a control system (e.g., control system 222 of FIG. 2). The leads 432 can couple power, communications or control signals. The leads 432 can, for example, provide for electrically conductive coupling, inductive coupling, capacitive coupling, optical coupling, galvanic coupling, fluidic coupling or thermal coupling by way of non-limiting example.

Figure 4G:
FIG. 4G is a top plan view according to yet another illustrated embodiment.
Figure 4H:
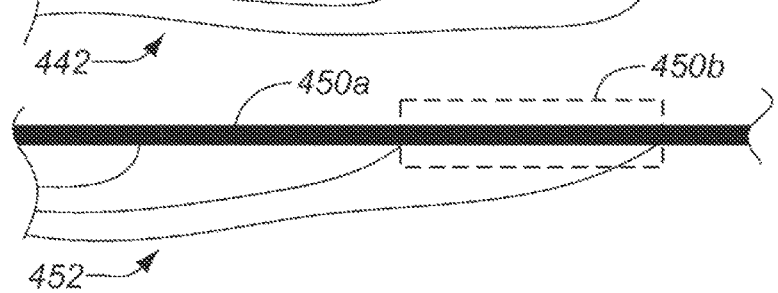
FIG. 4H is a top plan view according to yet another illustrated embodiment.

There are other approaches for creating transducer elements that do not rely on flexible circuit structures. FIGS. 4G and 4H provide examples of some of these.

FIG. 4G shows transducer elements 440a, 440b (collectively 440, only two called out in FIG. 4G) that are made from a bundle of carbon fibers. Leads 442 couple the transducer elements 440 to a control system.

FIG. 4H shows transducer elements 450a, 450b (collectively 450, only two called out in FIG. 4H) that are made directly from a hollow tube of a metal such as stainless steel or alternatively from wire. Leads 452 couple the transducer elements 450 to a control system.

The structures of the embodiments of FIGS. 4G and 4H may be advantageous in some embodiments, since the structures are relatively simple to assemble, and can be used directly as the supporting structure itself. Leads 442, 452 are connected at intervals to the carbon fiber or metal. The material between the leads 442, 452 form the transducer elements 440, 450. In order to function properly, these transducer elements 440, 450 should have electrical properties the same as, or similar to, the electrical properties indicated previously. These two embodiments provide an example of where the same transducer element 440, 450 can sense flow, sense or measure temperature, deliver the ablation energy, be an integral component of the supporting structure, or any combination of these functions.

FIGS. 4A-4H show examples of various transducer element configurations that can be employed in various embodiments. From the previous descriptions, it is important to note that a single transducer element can sense blood flow in order to distinguish between blood and tissue, sense an electrical potential of the tissue (e.g., heart wall), ablate tissue, sense or measure temperature, or form an integral component of the supporting structure, or any combination of these functions. The ablation may be performed by causing the transducer element to heat, or by delivering energy, such as radio-frequency (RF) energy directly to the tissue. Also, transducer elements can be constructed using individual leads, common ground leads, or shared leads. Each lead may have a separate lead that runs in parallel to it for the purpose of accurately determining voltage potential directly at the transducer element. As well, the examples discussed methods of sensing temperature that relied on changes in resistance. However, it is certainly possible to use other temperature sensing methods, such as thermistors or thermocouples in conjunction with the transducer elements that produce heat. For example, the sensing transducer element of the embodiment of FIG. 4A could be a thermistor, resistance temperature detector (RTD), thermocouple or temperature sensitive diode by way of non-limiting example. In some example embodiments, a transducer element (e.g., a resistance temperature detector) can be used to induce a temperature change as well as sensing the temperature change.

Figure 7:
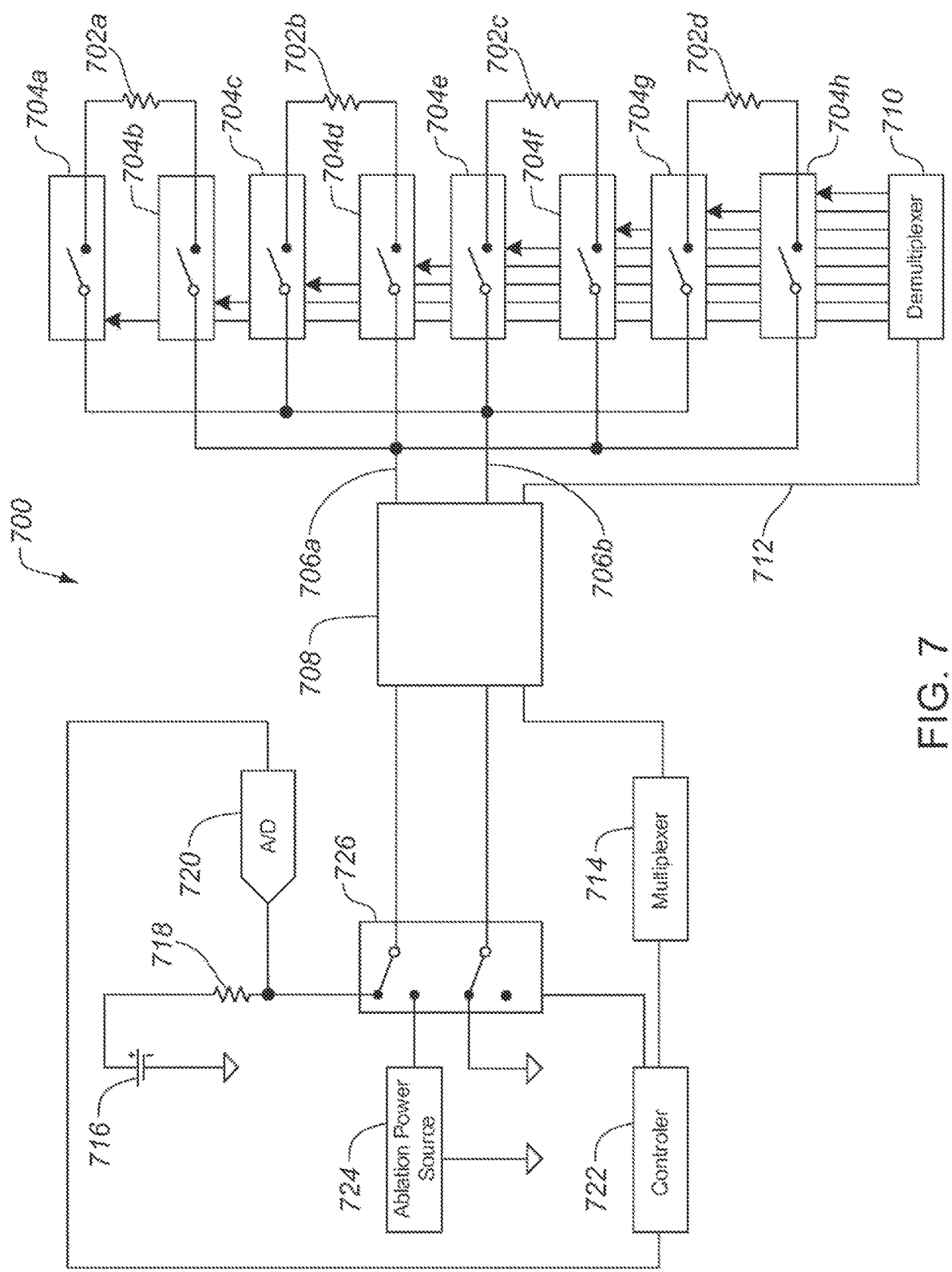
FIG. 7 is a circuit diagram of a system used for flow sensing, port location, and tissue ablation according to various example embodiments.

FIG. 7 schematically shows an embodiment of an electric circuit 700 that can be used to distinguish between blood and tissue within a bodily cavity by sensing blood flow.

In this example embodiment, transducer elements 702a-702d (collectively 702) may be resistive elements, for example formed from copper traces on a flexible printed circuit board substrate, or resistive wires mounted on a structure. Each transducer element 702 is connected by electronic transducer selection switches 704a-704h (collectively 704) to a single pair of conductors 706a, 706b (collectively 706) that provide a path out of the body via a cable 708. The transducer selection switches 704 may, for example be FET or MOSFET type transistors. The transducer selection switches 704 will typically need to carry significant power during the ablation phase. The cable 708 may extend through a lumen of a catheter (not shown) or may otherwise form part of a catheter structure.

The transducer selection switches 704 are selected by signals applied by a demultiplexer (selector) 710. The demultiplexer 710 may be controlled by a small number of conductors 712 (or even a single conductor if data is relayed in serial form). Conductors 706, 712 extend out of the body via the cable 708. The transducer selection switches 704 and the demultiplexer 710 may be built into a catheter (e.g., catheter 106 of FIG. 1) near a distal end or point of deployment. The transducer selection switches 704 and demultiplexer 710 may be located within or near the expandable frame (e.g., expandable frame 208 of FIG. 2 in order to minimize the number or length of the conductors extending through the catheter.

At the other or proximate end of the catheter are a mode selection switch 726 and multiplexer 714. The mode selection switch 726 is operable to select between a flow sensing mode (position shown in the drawing) and an ablation mode (second position of the mode selection switch 726). In flow sensing mode, a current is created by a voltage source 716 and resistor 718 (forming an approximate current source) and routed into a transducer element 702 selected via transducer selection switches 704. The two transducer selection switches 704 that are connected to a given one of the transducer elements 702 to be used to sense flow are set to be closed and the remainder of the transducer selection switches 704 are set to be open. The voltage drop across the transducer element 702 is measured via an analog-to-digital converter (ADC) 720 and led to a controller (i.e., control computer 722).

It may be advantageous to use alternating current or a combination of alternating current and direct current for sensing and ablation, for example, direct current for ablation and alternating current for sensing. Alternating current approaches may also prevent errors from electrochemical potentials which could be significant if different metals come in contact with blood.

Determination of the location of the bodily cavity ports can be achieved by turning on all of transducer elements 702 sequentially or in groups and determining a temperature by measuring the resistance of each transducer element 702. A map of the temperature of the transducer elements 702 may be formed in controller 722 or the controller 722 may otherwise determine a position or orientation (e.g., pose) or both the position and orientation of the device in the cavity. The transducer elements 702 with lower temperatures can correspond to ports leading to the veins or valves when the bodily cavity is an intra-cardiac cavity such as a left atrium.

When mode selection switch 726 is set to select ablation, an ablation power source 724 is connected sequentially to the transducer elements 702 that are selected by the controller 722 by addressing the multiplexer 714, which in turn controls the transducer selection switches 704 via the demultiplexer 710. The ablation power source 724 can be an RF generator, or it can be one of several other power sources, several of which are described below. If ablation power source 724 is an RF generator, the configuration of FIG. 7 implies unipolar RF ablation, in which current is fed into the tissue and passes to a ground (i.e., also referred to as an indifferent electrode) connected to the body. The current that passes through the tissue causes the tissue to heat. However, bipolar ablation can be used as well. During bipolar ablation, current passes from a first one of the transducer elements 702 through the tissue to a second one of the transducer elements 702. In some embodiments, each of the first one of the transducer elements 702 and the second one of the transducer elements 702 is provided on a different flexible circuit strip during the bipolar ablation. In some embodiments, the first one of the transducer elements 702 is provided on a flexible circuit strip that is spatially separated from a flexible circuit strip that the second one of the transducer elements 702 is provided on during the bipolar ablation. In some embodiments, the first one of the transducer elements 702 is provided on a portion of a support frame that is spatially separated from a portion of the support frame that the second one of the transducer elements 702 is provided on during the bipolar ablation. A first one of the transducer elements 702 may be provided on a portion of a support frame that is spatially separated by a spatial region from a portion of the support frame that a second one of the transducer elements 702 is provided on, the spatial region not including any physical portion of the support frame. Other sources of ablation can be used besides radio-frequency sources. Frequencies from DC to microwaves can be used, as well as delivery of laser power via optical fibers or cryogenics via thin tubes. For laser ablation, the transducer selection switches 704 may fake the form of optical switches. For cryogenic ablation, the transducer selection switches 704 may take the form of suitable valves or actuators (e.g., solenoids). Alternatively, the bottom terminal of the lower switch of mode selection switch 726 may be coupled directly to ground. In this configuration, the ablation power source 724 can be configured to supply current with frequencies from DC to microwave, which will cause the selected transducer elements 702 to heat directly and produce ablation via thermal conduction.

During ablation it may be desirable to monitor the temperature of the tissue that forms the interior surface of the bodily cavity. The ideal temperature range for the tissue during ablation is typically 50-100 C.° in some embodiments. Since this example embodiment includes temperature monitoring as part of the blood flow sensing, the progress of ablation can be monitored by temporarily switching mode selection switch 726 to a temperature sensing position several times during the ablation.

Figure 6:
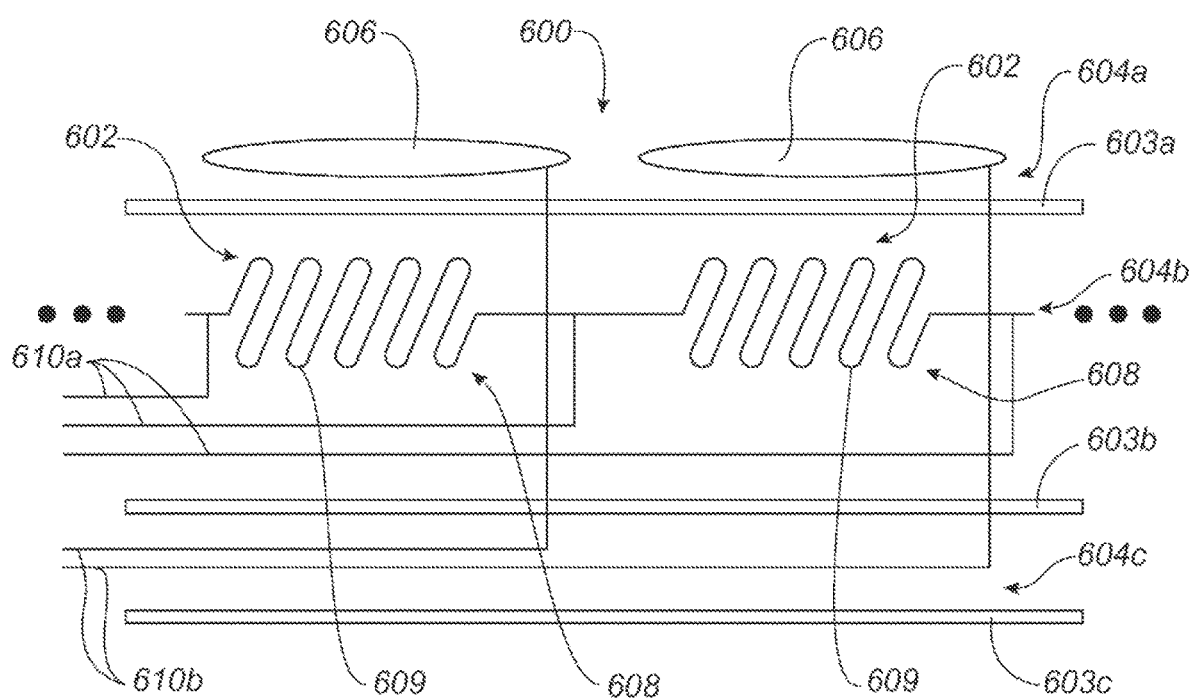
FIG. 6 is a schematic view of a flexible circuit structure employed to provide a plurality of transducer elements according to an example embodiment.

FIG. 6 is a schematic view of a flexible circuit structure 600 employed to provide a plurality of transducer elements 602 (two called out) according to an example embodiment. Flexible circuit structure 600 can be formed by various techniques including flexible printed circuit techniques. In this example embodiment, flexible circuit structure 600 includes various layers including flexible layers 603a, 603b and 603c (i.e., collectively flexible layers 603). In this example embodiment, each of flexible layers 603 includes or consists of at least one electrical insulator material (e.g., polyimide). One or more of the flexible layers 603 can include a different material than another of the flexible layers 603. In this example embodiment, various ones of electrically conductive layers 604a, 604b and 604c (collectively electrically conductive layers 604) are interposed between or interleaved with the flexible layers 603. In this example embodiment, each of the electrically conductive layers 604 is deposited or patterned to form various electrically conductive members. For example, electrically conductive layer 604a is deposited or patterned to form a respective electrode 606 (two called out) of each of the transducer elements 602. Electrically conductive layer 604b is deposited or patterned to form respective temperature sensors 608 for each of the transducer elements 602 as well as various traces or leads 610a arranged to provide electrical energy to the temperature sensors 608. In this example embodiment, each temperature sensor 608 includes a deposited or patterned resistive member 609 (two called out) having a predetermined electrical resistance. In this example embodiment, each resistive member 609 includes a metal having relatively high electrical conductivity characteristics (e.g. copper). In this example embodiment, electrically conductive layer 604c is deposited or patterned to provide portions of various traces or leads 610b arranged to provide an electrical communication path to electrodes 606. In this example embodiment, traces or leads 610b are arranged to pass though vias (not shown) in flexible layers 603a and 603b to couple with electrodes 606.

In various example embodiments, electrodes 606 are employed to selectively deliver RF energy to various tissue structures within an intra-cardiac cavity (not shown). In various example embodiments, each electrode 606 is employed to sense an electrical potential in the tissue proximate the electrode 606. In various example embodiments, each electrode 606 is employed in the generation of an intra-cardiac electro gram. In this example embodiment, each resistive member 609 is positioned directly adjacent a respective one of the electrodes 606. Each resistive member 609 is positioned in a stacked or layered array with a respective one of the electrodes 606 to form a respective one of the transducer elements 602. In this example embodiment, the resistive members 609 are connected in series to allow electrical current to pass through all of the resistive members 609. In this example embodiment, traces or leads 610a are arranged to allow for a sampling of electrical voltage between associated resistive members 609. This arrangement allows for the electrical resistance of each resistive member 609 to be accurately measured.

Figure 8A:
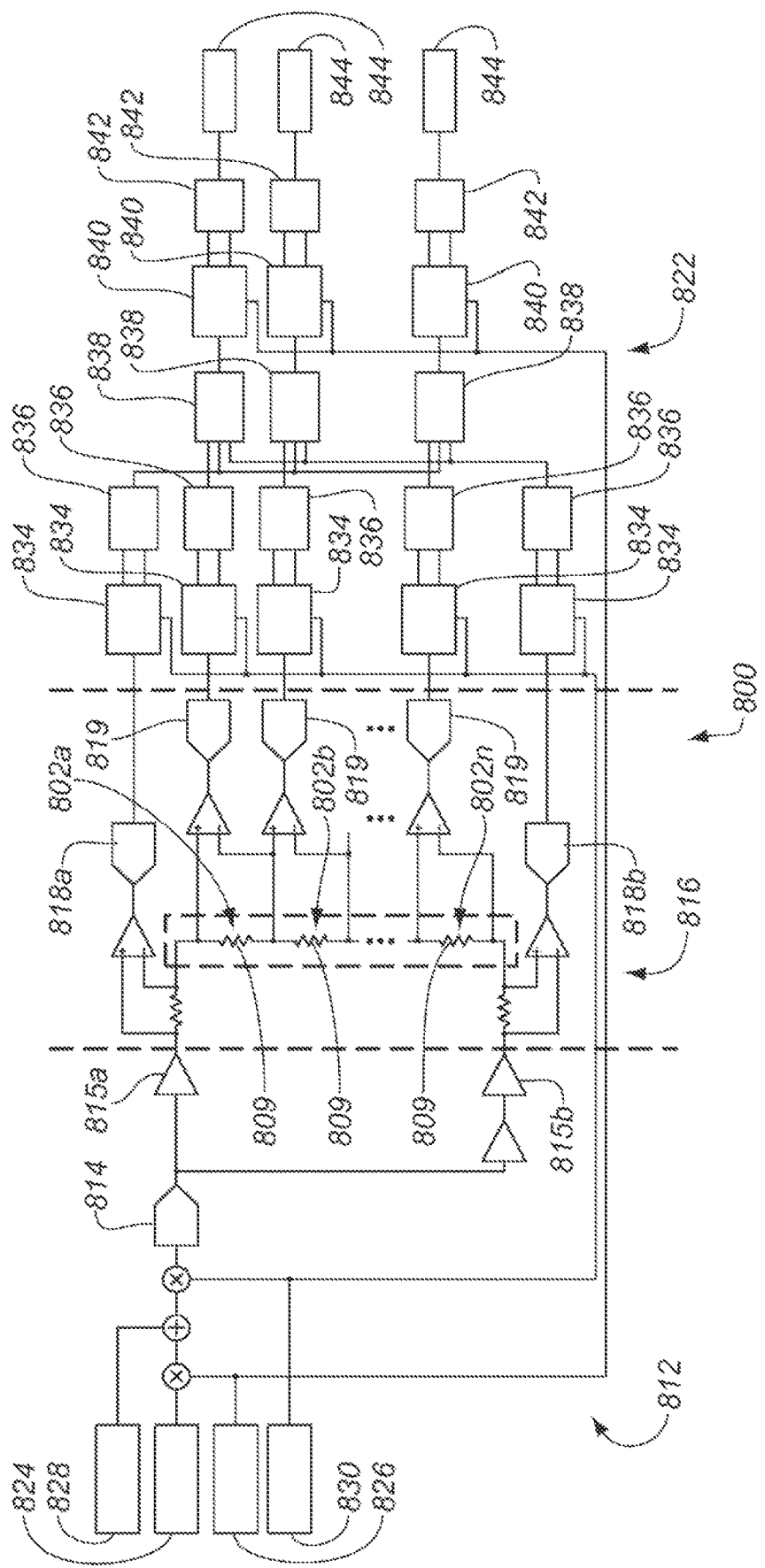
FIG. 8A is a block diagram of an electrical circuit that can be used to determine a resistance of various resistive members employed by various transducer elements in various example embodiments.

FIG. 8A is a block diagram of an electrical circuit 800 that can be used to determine an electrical resistance of various resistive members (e.g., resistive members 609) employed by various transducer elements (e.g., transducer elements 602) in various example embodiments. In this example embodiment, a plurality of transducer elements 802a, 802b . . . 802n (collectively 802) can be positioned on a structure (e.g. frame 208) that is configurable between an unexpanded or delivery configuration in which the structure is suitably sized for percutaneous delivery to a bodily cavity (e.g., left atrium 104) having one or more ports (e.g., pulmonary vein ostiums (not shown) or a mitral valve 126) in fluid communication with the bodily cavity and an expanded or deployed configuration in which the transducer elements are repositioned within the bodily cavity. In some embodiments, the structure may be too large for percutaneous delivery to the bodily cavity in the expanded/deployed configuration. At least a first transducer element 802 can be spaced on the structure from a second transducer element 802 such that at least the first transducer element 802 is positioned on a portion of the structure lying across a portion of one of the one or more ports and the second transducer element 802 of the plurality of transducer elements 802 is positioned on a portion of the structure which does not overlie the one of the one or more ports when the structure is in the expanded/deployed configuration. The number of transducer elements 802 employed can vary in different embodiments.

Figure 8B:
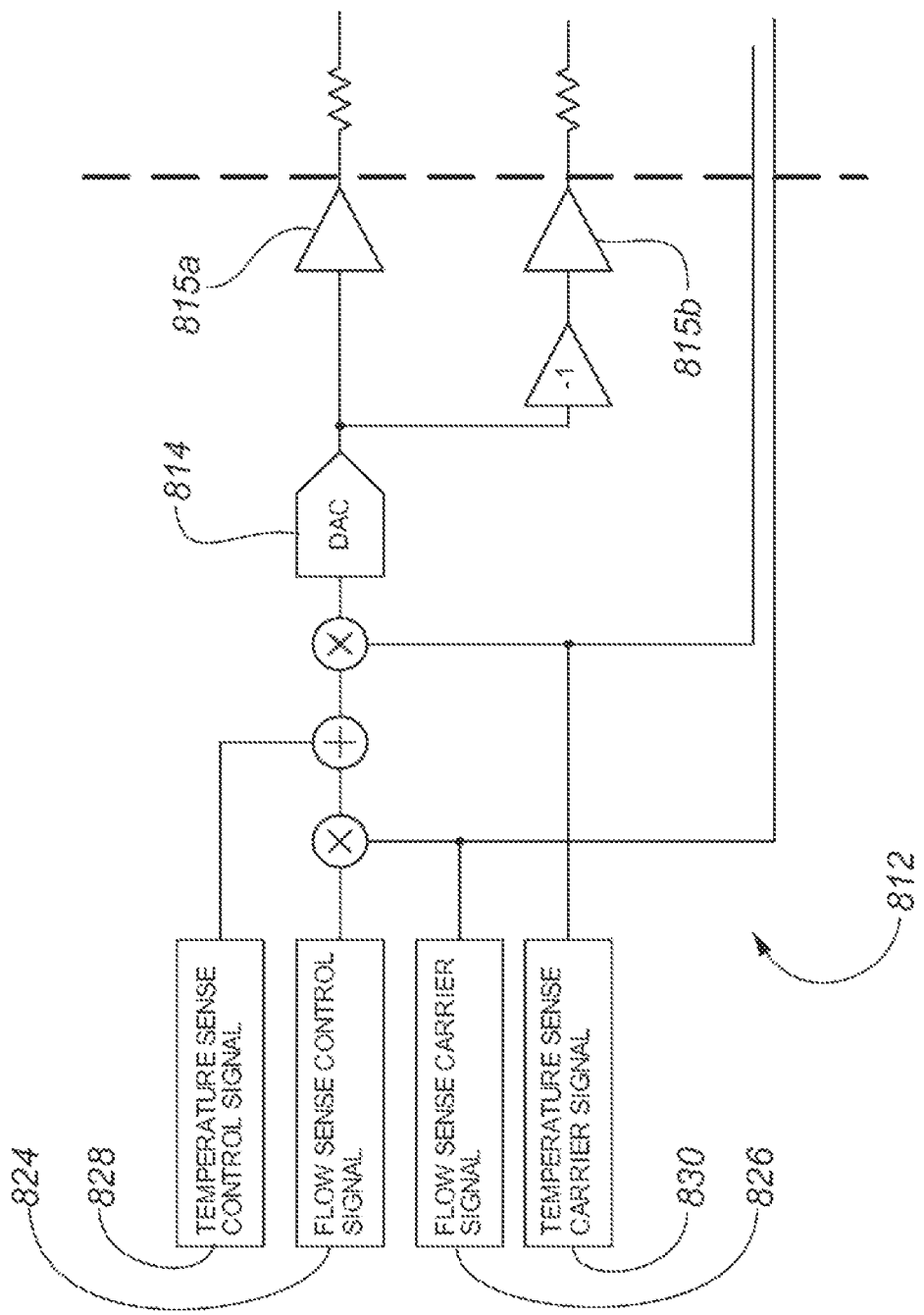
FIG. 8B is an enlarged view of a signal source module of the block diagram of FIG. 8A.
Figure 8C:
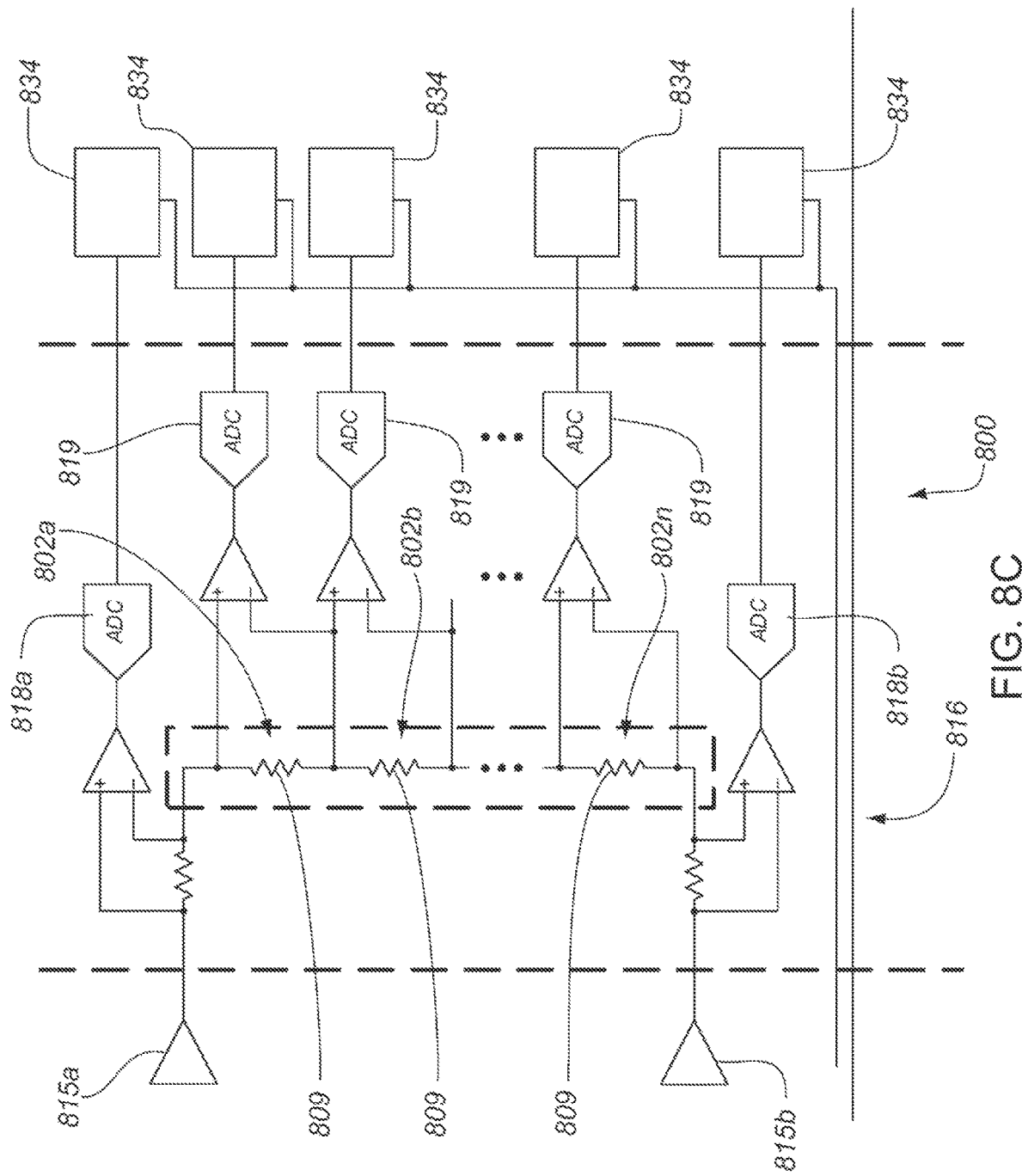
FIG. 8C is an enlarged view of a sensing system module of the block diagram of FIG. 8A.

In this example, each transducer element 802 includes a respective resistive member 809 (three called out in FIG. 8A), for example formed from copper traces on a flexible printed circuit board substrate, or resistive elements provided on a structure. Each transducer element 802 is driven by a state machine (not shown) within controller 822. In this example embodiment, electrical circuit 800 includes a signal source 812 (i.e., an enlarged view shown in FIG. 8B), a sensing system 816 (i.e., an enlarged view shown in FIG. 8C) and controller 822 (i.e., an enlarged view shown in FIG. 8D), each schematically distinguished from one another by broken lines for clarity. It is understood that each of signal source 812, sensing system 816 and controller 822 may each include different circuitry than those shown in FIG. 8A and respective ones of FIGS. 8B, 8C and 8D.

In this example embodiment, signal source 812 is used to provide various signals. In some embodiments, signal source 812 provides at least one signal having a number of alternating "HIGH" and "LOW" periods within a predetermined time duration. One set of HIGH and LOW periods may define a duty cycle in some embodiments. Each of at least one of the HIGH periods and the LOW periods may include a plurality of periodic continuous signals. It is understood that signal source 812 can provide signals having other waveforms in other embodiments.

In some embodiments, signal source 812 provides various input signals to at least some of the transducer elements 802 during a temperature sensing mode. In some embodiments, signal source 812 provides various input signals to at least some of the transducer elements 802 during a flow sensing mode. In some example embodiments, signal source 812 provides various input signals to each of the transducer elements 802 during a mapping mode in which information specifying a location of various anatomical features within a bodily cavity is provided. For example, information specifying a location of each of one or more regions of an interior tissue surface within an intra-cardiac cavity may be provided along with information specifying a location of each of at least one of one or more ports on the interior tissue wall with respect to the one or more regions during the mapping mode. In some example embodiment, signal source 812 provides various input signals during an ablation mode.

Signal source 812 can include one or mote sources configured to provide a set of one or more signals. In this example embodiment, a state machine (not shown) in controller 822 may be employed to cause various control signals (not shown) to be provided to signal source 812 to configure electrical circuit 800 in at least one of a temperature sensing mode and a flow sensing mode. In some example embodiments, signal source 812 includes an ablation source (e.g., ablation source 724) coupled to transfer energy to, or from, the tissue wall via one or more transducers. The coupling may for example be an electrical or thermal direct connection or indirect connection. In some example embodiments, signal source 812 includes a radio frequency generator arranged to provide a varying electrical current to at least one of the transducer elements 802 to provide energy to tissue from the at least one of the transducer elements 802.

In this illustrated embodiment, digital-to-analog converter (DAC) 814 generates an input signal that is amplified and is driven across the series of the connected resistive members 809 during a temperature sensing mode. Amplifiers including driver 815a and driver 815b are arranged to produce a balanced output across the series of connected resistive members 809. Electrical current driven through resistive members 809 is sampled by sensing system 816. In this example embodiment, electrical current driven through resistive members 809 is sampled at each of the drivers 815a, 815b via respective ones of analog-to-digital converters (ADC) 818a, 818b. It is noted that sensing the electrical current at each of the drivers 815a, 815b can allow the system to detect possible failures that may result in the electrical current leaking through another path. Voltage across each of the resistive members 809 is also sampled by sensing system 816 via respective ones of analog-to-digital converters (ADC) 819 (three called out in each of FIGS. 8A and 8C). In this example embodiment, the current and voltage measurements are sampled synchronously with the input signal and the demodulation of each measurement is computed by controller 822. Electrical circuit 800 allows for the electrical resistance of each of the resistive members 809 to be precisely measured. The resistance of an electrically conductive metal (e.g., copper) changes based on the temperature of the electrically conductive metal. The rate of change is denominated as a temperature coefficient of resistance (TCR). The resistance of various ones of the resistive members 809 may be related to the temperature of the resistor element 809 by the following relationship:

$$R = R_0 * [1 + TCR * (T - T_0)], \text{ where:}$$

R is a resistance of the electrically conductive metal at a temperature T;

$R_0$ is a resistance of the electrically conductive metal at a reference temperature $T_0$;

TCR is the temperature coefficient of resistance for the reference temperature (i.e., the TCR for copper is 4270 ppm at $T_0$=0° C.); and T is the temperature of the electrically conductive metal.

In this example embodiment, flow sensing is measured by electrical circuit 800 by measuring the rate of convective cooling at various ones of the resistive members 809. In this example embodiment, when the flow sensing mode is enabled, various ones of the resistive members 809 whose temperature is measured during the temperature sensing mode can also be employed to deliver energy (i.e., heat) during the flow sensing mode. In this example embodiment, the energy is delivered using the same drivers 815a, 815b employed in the temperature sensing mode. It is understood that additional and or alternate drivers may be employed in other example embodiments but with additional cost and complexity. When the temperature sensing mode is not active, the state machine in controller 822 continues to drive an input signal to each of the resistive members 809 in this example embodiment.

In this example embodiment, a flow sense control signal 824 is employed to enable or disable flow sensing capability. In this example embodiment, flow sense control signal 824 is modulated using flow sense carrier signal 826. In some embodiments, flow sense carrier signal 826 can include a number of alternating "HIGH" and "LOW" periods within a predetermined time duration. Respective sets of adjacent HIGH and LOW periods may define a duty cycle. Each of at least one of the HIGH periods and the LOW periods may include a plurality of periodic continuous signals. In this example embodiment, flow sense control signal 824 is modulated using a 1-Hertz (Hz) square-wave flow sense earner signal 826. It is understood that the flow sense carrier signal 826 can include other waveforms in other example embodiments. In this example embodiment, the resulting signal is summed with a temperature sense control signal 828 which introduces a relatively small signal that allows temperature to be sensed regardless of the state of the flow sense control signal 824. In this example embodiment, the combined temperature sense control signal 828 and modulated flow sense control signal 824 is further modulated using a 25 kHz square wave temperature sense carrier signal 830. The additional modulation may be motivated for various reasons. For example, the additional modulation may be performed to ensure that the patient is not exposed to low frequency signals. Temperature sense carrier signal 830 may include other waveforms in other example embodiments.

In this example embodiment, a 25 kHz input signal (not shown) results and is provided by signal source 812 across each of the resistive members 809. In this example embodiment, electrical current passing through resistive members 809 is sampled at each of the drivers 815a, 815b via respective ones of analog-to-digital conveners (ADC) 818a and 818b. Voltage across each of the resistive members 809 is also sampled via respective ones of analog-to-digital converters (ADC) 819. In various example embodiments, a respective first signal set of one or more signals is provided by each transducer element 802 to controller 822. In this example embodiment, each respective first signal set includes a signal representative of a measured voltage across a respective one of the resistive members 809 as sensed by sensing system 816. At least one signal representative of a measured electrical current through each respective resistive member 809 is also provided by sensing system 816 to controller 822.

Figure 8D:
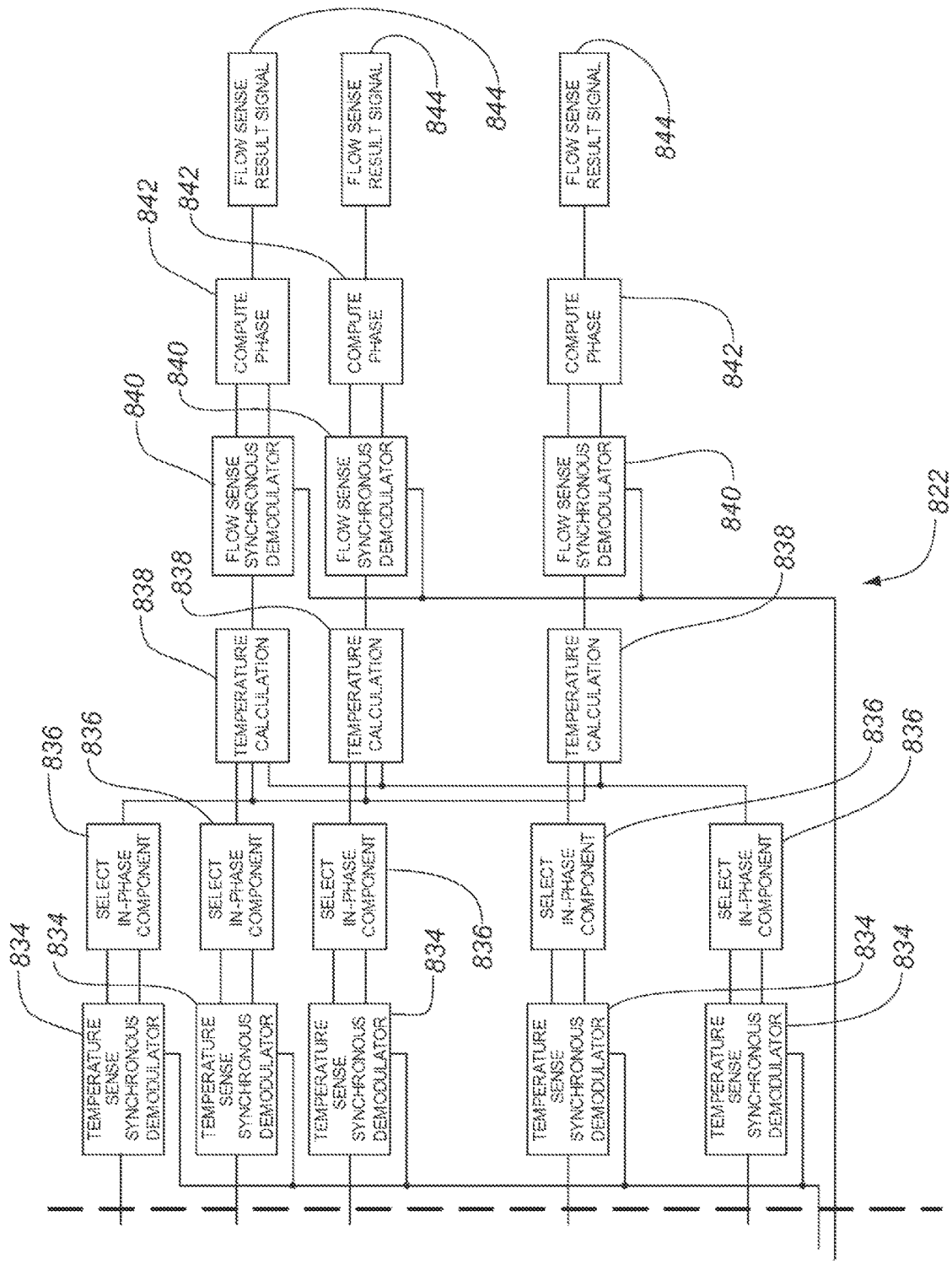
FIG. 8D is an enlarged view of a controller module of the block diagram of FIG. 8A.

In this example embodiment, each of the signals representative of the measured electrical currents and voltages associated with each transducer element 802 are demodulated synchronously with the temperature sense carrier signal 830 by a respective synchronous demodulator 834 (five called out in each of FIGS. 8A and 8D). It is noted that although signals provided via respective ones of analog-to-digital converters (ADC) 818*a* and 818*b* are also demodulated synchronously with the temperature sense carrier signal 830 by a respective synchronous demodulator 834 in this illustrated embodiment, other different synchronous demodulators may be used in other embodiments. In this example embodiment, each of a plurality of controller modules 836 (five called out in each of FIGS. 8A and 8D) selects the in-phase component of a respective one of the various demodulated signals. In this example embodiment, various controller modules 838 (three called out in each of FIGS. 8A and 8D) processes various sets of the in-phase components to determine electrical resistance information for each of the resistive members 809. In this example embodiment, controller modules 838 further process the electrical resistance information to determine temperature information for each of the resistive members 809.

In this example embodiment, a synchronous demodulator 840 (three called out in each of FIGS. 8A and 8D) is employed to synchronously demodulate a signal including or encoding temperature information associated with a respective one of the resistive members 809 with the flow sense carrier signal 826. In some example embodiments, a synchronous demodulator 840 (three called out in each of FIGS. 8A and 8D) is employed to synchronously demodulate a signal including electrical resistance information associated with a respective one of the resistive members 809 with the flow sense carrier signal 826. In this example embodiment, controller module 842 (three called out in each of FIGS. 8A and 8D) is used to determine phase information of the demodulated signal provided by a respective one of the synchronous demodulators 840. In this example embodiment, the phase information is provided by a respective flow sense result signal 844 (three called out in each of FIGS. 8A and 8D) provided by the controller module 842.

In this example embodiment, each controller module 842 determines information representing the phase of a first signal derived at least in part from the first signal set provided by a respective one of the transducer elements 802 relative to a phase of a second signal (e.g., flow sense carrier signal 826 in this illustrated embodiment) of a respective second signal set provided by signal source 812. In various example embodiments, signal source 812 provides a respective input signal to each transducer element 802, and sensing system 816 provides a respective set of one more response signals (e.g., voltage and current signals in this example embodiment) responsive to at least a temperature change at least proximate to the respective transducer element 802. In these various embodiments, controller 822 derives at least one signal from each set of one or more response signals and determines a respective set of one or more values representative of a phase difference between each derived at least one signal and the respective input signal provided to the transducer element 802 associated with the set of one or more response signals. In some of the various embodiments (e.g., this example embodiment), signal source 812 provides a same input signal to each of the transducer elements 802. In some of the various embodiments, each respective input signal provided by signal source 812 to at least one of the transducer elements 802 has a predetermined phase difference relative to the respective input signal provided to another of the transducer elements 802. In some of the various embodiments, signal source 812 provides a plurality of signals, at least one of the signals having a predetermined phase difference relative to another of the plurality of signals. In some of the various embodiments, controller 822 determines the respective set of one or more values representative of a phase difference between each derived at least one signal and rive respective input signal provided to the transducer element 802 associated with the set of one or more response signals based on a reference signal having a predetermined phase relative to the respective input signal provided to the transducer element 802 associated with the set of one or more response signals.

In various example embodiments in which the plurality of transducer elements 802 are arranged within a bodily cavity (e.g., an intra-cardiac cavity such as a left atrium) having various internal anatomical features, controller 822 can provide information specifying a location of at least one of the internal anatomical features within the bodily cavity based at least in part on the phase information of the demodulated signal provided by a respective one of the synchronous demodulators 840. As an example, the plurality of transducer elements 802 may be arranged within a bodily cavity (e.g., an intra-cardiac cavity such as a let) atrium 104) defined at least in part by a tissue wall having an interior tissue surface interrupted by one or more ports in fluid communication with the bodily cavity (e.g., pulmonary veins). In such an example, the controller 822 can provide information specifying a location of each of one or more regions of the interior tissue surface and a location of at least one of the one or more ports on the interior tissue surface with respect to the one or more regions. The information may be determined by controller 822 based at least in part on the phase of a first signal derived at least in part from a first signal set provided by respective ones of the transducer elements 802 relative to a phase of a second signal (i.e., flow sense carrier signal 826 in this illustrated embodiment) of a respective second signal set provided by signal source 812. In various example embodiments in which signal source 812 provides a respective input signal to each transducer element 802 and sensing system 816 provides a respective set of one more response signals (i.e., voltage and current signals in this example embodiment) responsive to at least a temperature change at least proximate to the transducer element 802, controller 822 can provide information specifying a location of each of one or more regions of the interior tissue surface and a location of at least one of the one or more ports on the interior tissue surface with respect to the one or more regions. The provided information may be based at least in part on information including a respective set of one or more values representative of a phase difference between at least one signal derived from each respective set of one or more response signals and the respective input signal provided to the respective transducer element 802 associated with the set of one or more response signals. In some embodiments, controller 822 provides information specifying a location of each of one or more regions of the interior tissue surface and a location of at least one of the one or more ports on the interior tissue surface with respect to the one or more regions in the form of a map. In some example embodiments, controller 822 provides a visual representation of the phase of each signal derived from various signals provided by sensing system 816 relative to the phase of a respective signal provided by the set of one or more signals outputted by signal source 812. Various displays or other output devices or system (e.g., display 232) may be employed to provide information from controller 822 to a user (e.g., a health care provider).

The present inventors have noted that when a signal source applies energy to a resistive element (e.g., resistive member 809 employed by various transducer elements 802) positioned within a medium having relatively high flow conditions, for example whet subjected to blood flow conditions proximate to a pulmonary vein port in the left atrium of a heart, the resistive element will heat to a lower temperature and will settle more quickly than if the resistive element were to be positioned within a medium having relatively low flow conditions, for example when positioned proximate to, or in contact with a region of a tissue surface within a left atrium positioned away from the pulmonary vein port. Likewise, when the signal source ceases to apply energy, the resistive element positioned within a medium having relatively high flow conditions will cool faster and will return to ambient temperature faster than if the resistive element were to be within a medium having relatively lower flow conditions. When the signal source repetitively applies and ceases to apply energy to the resistive element, the resulting temperature changes of the resistive element positioned in a medium having relatively low flow conditions will appear to have phase delay compared to the resulting temperature changes of the resistive element when positioned in a medium having relatively higher flow conditions.

EXAMPLES

The following are examples of various example embodiments. It is understood that other embodiments are not so limited, as alternative embodiments have been provided and will become readily apparent to those of ordinary skill in the art.

A device having a framed structure made up of a plurality of elongate members arranged in an expanded configuration similar to that illustrated in FIGS. 1 and 2 was employed in these examples. Each elongate member was made up of a resilient metallic material (e.g., stainless steel) sheathed in an electrical insulator material (i.e., polyimide). Attached to each of a subset of four (4) of the elongate members, denominated herein as elongate members #1, #2, #3 and #4 (at least some referred to in some of the graphs provided by FIGS. 10, 11 and 12), was a respective flexible circuit structure (i.e., similar to that shown in FIG. 6). Each flexible circuit structure provided nine (9) transducer elements, each transducer element including a resistive member (i.e., similar to resistive members 609), with power arranged to be selectively provided to each resistive member. The device was inserted into a water bath and a multi-hole nozzle was arranged to selectively establish flow conditions within the bath. The nozzle was controlled to selectively expose the resistive members to a relatively low flow condition (i.e., essentially a stagnant bath) herein referred to as a "No Flow" condition and a relatively high flow condition herein referred to as a "Flow" condition. Various ones of resistive members were spatially arranged to experience different degrees of the flow in the Flow condition. In this example embodiment, power provided to each resistive member was modulated in each of the Flow and No Flow conditions. Each modulated cycle included a period where constant modulated voltage was applied to each resistive member followed by a period where minimal voltage was provided to the resistive member (i.e., voltage sufficient to measure the resistance with minimal heating). Each resistive member was subject to voltages that were varied between three (3) levels (i.e., 2V, 4V and 8V), each level provided at each of a signal frequency that was varied between three (3) levels (i.e., 0.5 Hz, 1 Hz and 5 Hz) in each of the Flow and No Flow conditions. An electrical resistance plot for each resistive member was produced for each of these various power conditions.

Figure 9A:
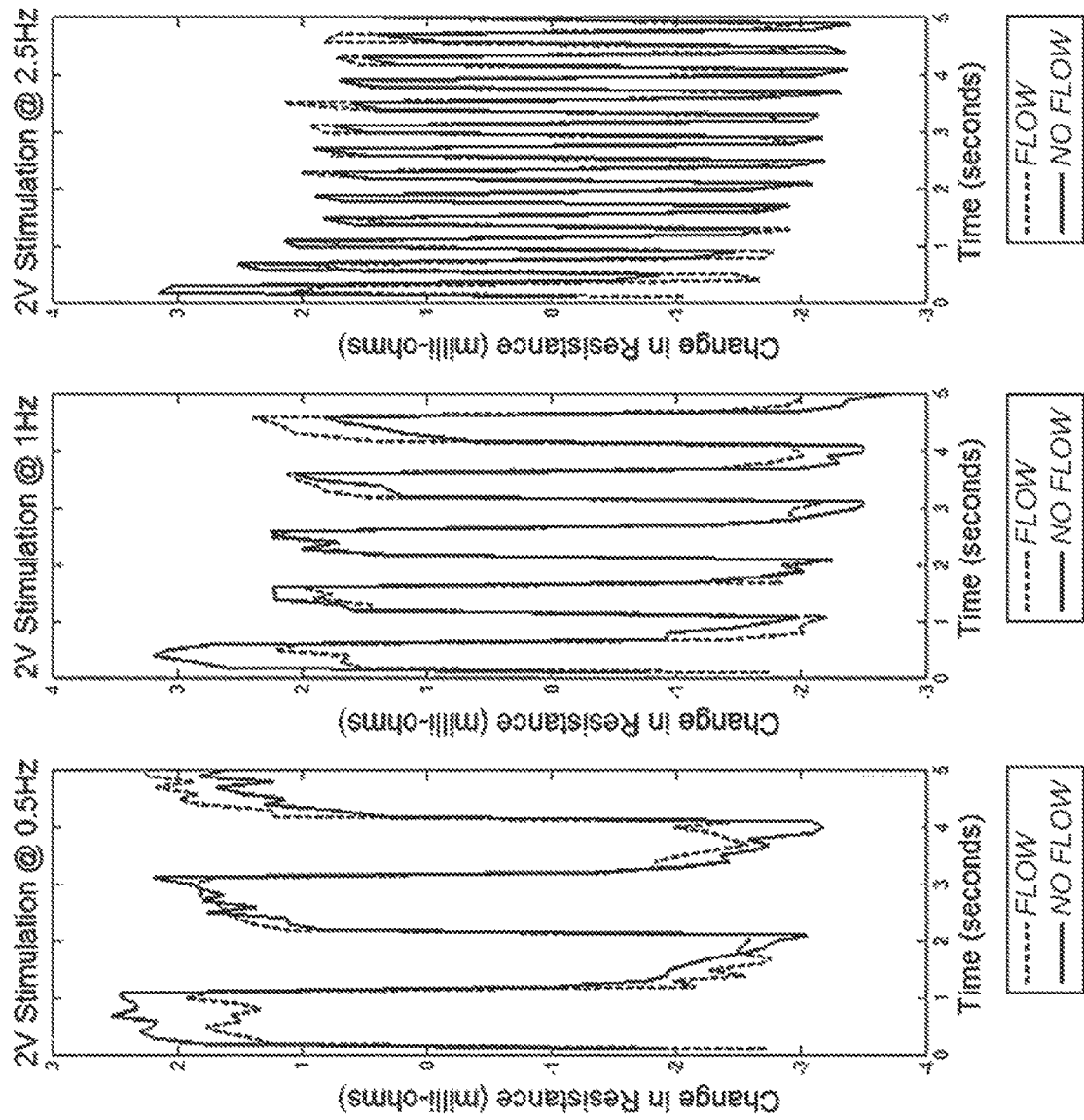
FIG. 9A is a series of graphs or plots of change in resistance versus time of a resistive member in each of "Flow" and "No Flow" conditions at respective frequencies responsive to a first input condition according to various example embodiments.
Figure 9B:
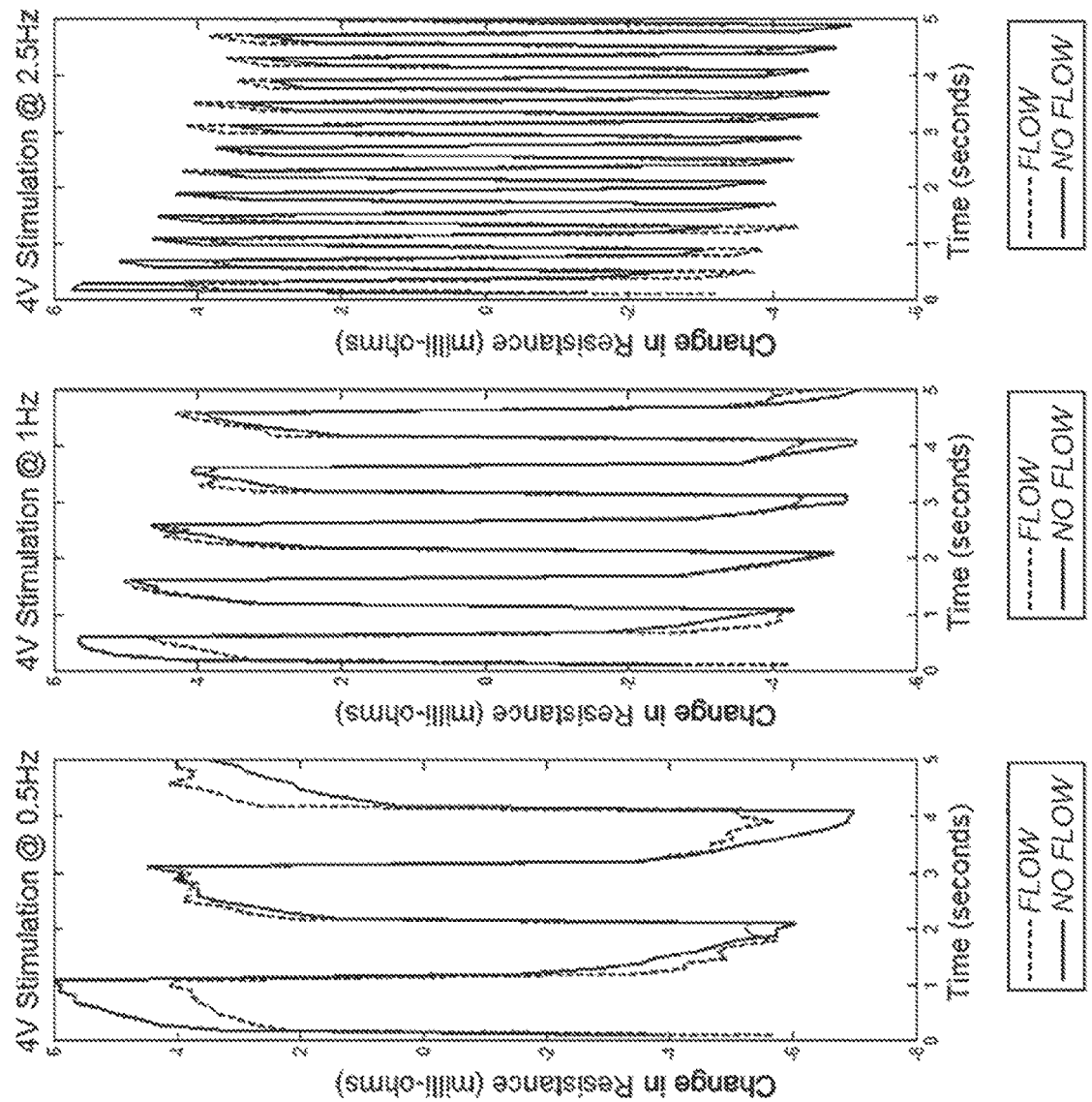
FIG. 9B is a series of graphs or plots of change in resistance versus time of the resistive member in each of "Flow" and "No Flow" conditions at respective frequencies responsive to a second input condition according to various example embodiments.
Figure 9C:
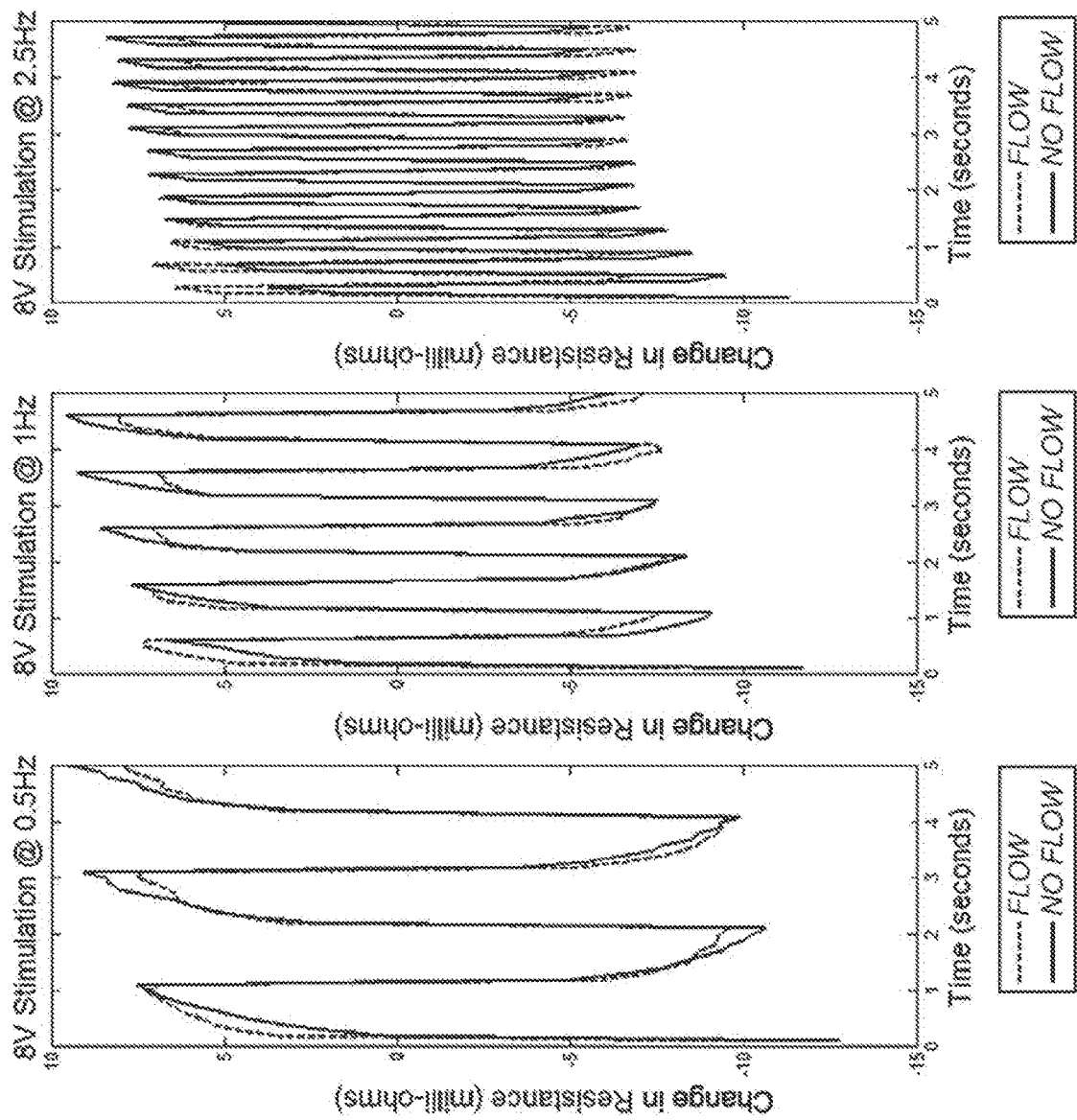
FIG. 9C is a series of graphs or plots of change in resistance versus time of the resistive member in each of "Flow" and "No Flow" conditions at respective frequencies responsive to a third input condition according to various example embodiments.

FIGS. 9A, 9B and 9C show a series of graphs or plots of change in resistance (in milli-ohms) over a selected number of time periods (in seconds) of one of the resistive members in each of the Flow and No Flow conditions under the influence of various voltage signals. Specifically, FIG. 9A includes respective graphs or plots of change in resistance versus time of a resistive member in response to an application of electrical power (e.g., voltage and/or current) at each of 2 V, 0.5 Hz; 2 V, 1 Hz; and 2 V, 2.5 Hz conditions. FIG. 9B includes graphs or plots of change in resistance versus time of the resistive member in response to an application of power at each of 4 V, 0.5 Hz; 4 V, 1 Hz; and 4 V, 2.5 Hz conditions. FIG. 9C includes graphs or plots of change in resistance versus time of the resistive member in response to an application of power at each of 8 V, 0.5 Hz; 8 V, 1 Hz; and 8 V, 2.5 Hz conditions. In this example embodiment, the Flow conditions are represented by the broken line traces while the No Flow conditions are represented by the continuous line traces. Upon initial inspection of the graphs or plots there appears to be little discrimination between the traces representing the flow conditions and their corresponding traces representing the No Flow conditions. Some of the traces representing the Flow conditions for various ones of the 0.5 Hz and 1 Hz cases generally appear to have a somewhat squarer shape than their corresponding traces representing the No Flow conditions. In this example embodiment, a frequency domain transform was employed to further distinguish the traces. In this example embodiment, a Fourier power series was applied over an integral number of periods. The magnitude and phase response of the Flow and No Flow cases for each of the resistive members was compared. For each frequency, the number of periods was chosen as the least common multiple between all of the periods to allow each power series to use the same number of samples. The results for various ones of the resistor elements are provided in the following examples.

Example 1

Figure 10A:
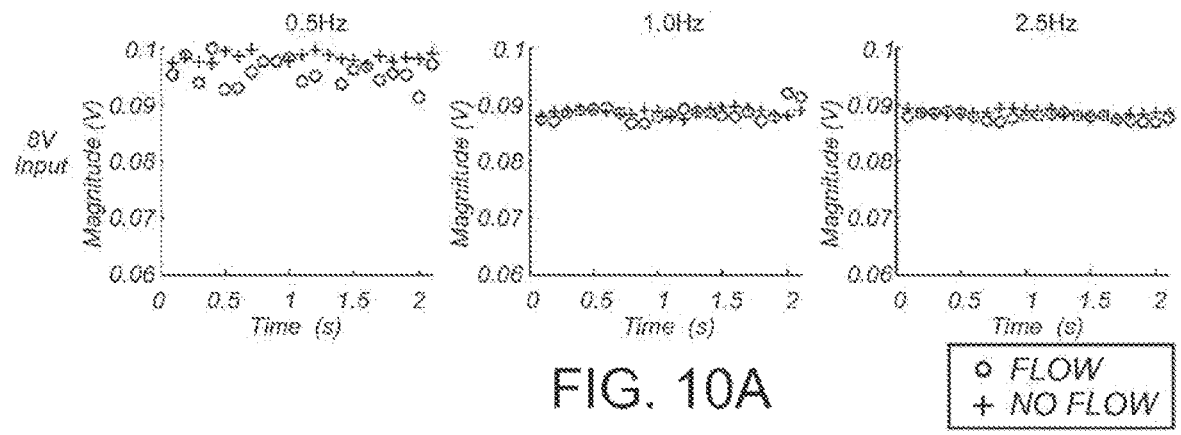
FIG. 10A is a graph or plot of a Fourier power series magnitude versus time for a first resistive member under "Flow" and "No Flow" conditions for an 8-volt input voltage signal.
Figure 10B:
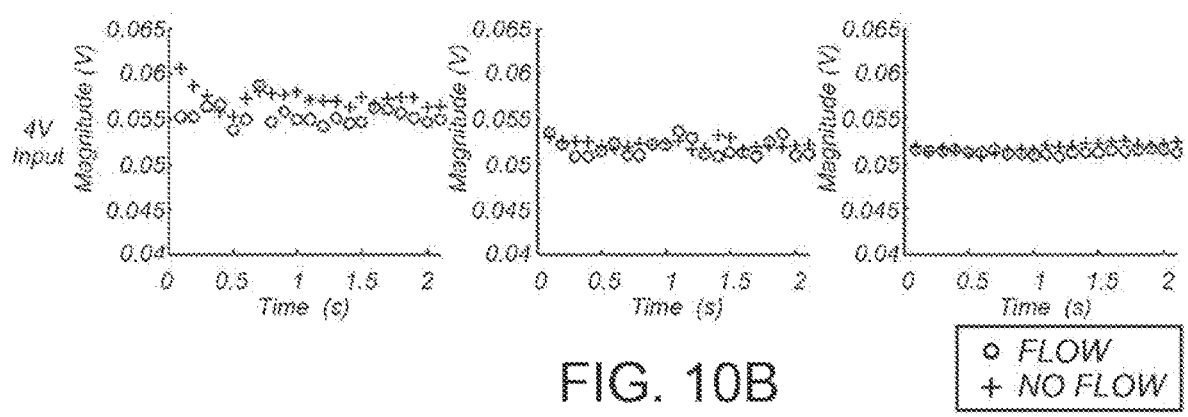
FIG. 10B is a graph or plot of a Fourier power series magnitude versus time for the first resistive member under "Flow" and "No Flow" conditions for a 4-volt input voltage signal.
Figure 10C:
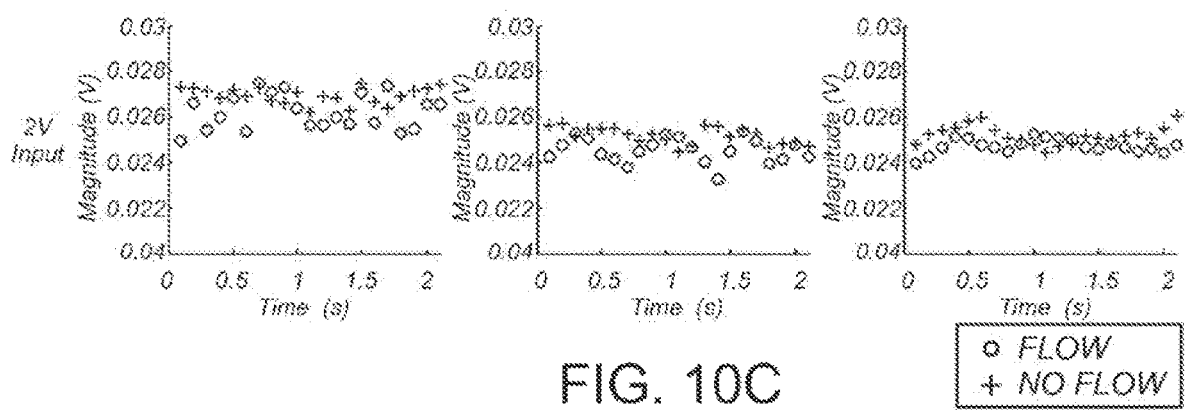
FIG. 10C is a graph or plot of a Fourier power series magnitude versus time for the first resistive member under "Flow" and "No Flow" conditions for a 2-volt input voltage signal.
Figure 10D:
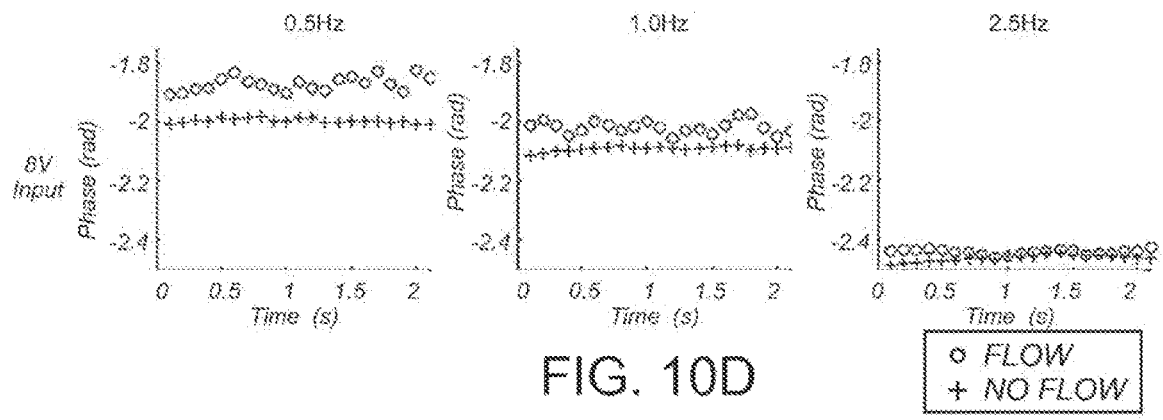
FIG. 10D is a graph or plot of a Fourier power series phase versus time for the first resistive member under "Flow" and "No Flow" conditions for an 8-volt input voltage signal.
Figure 10E:
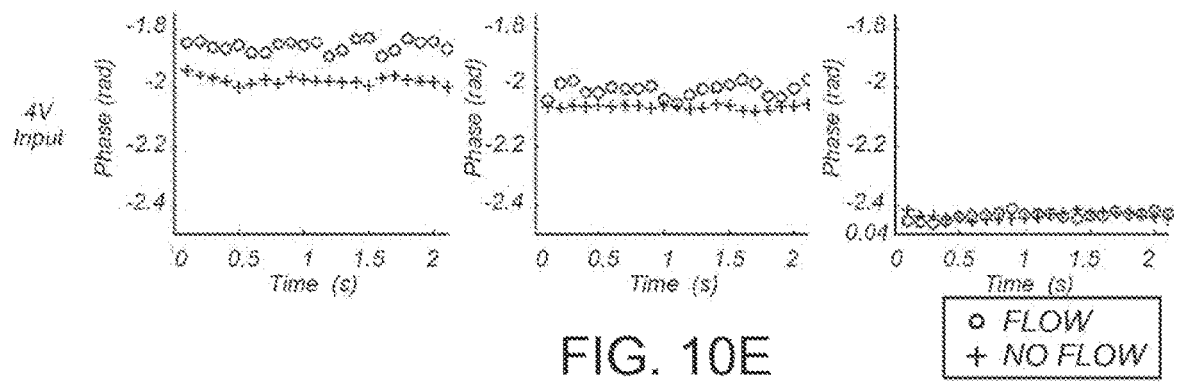
FIG. 10F is a graph or plot of a Fourier power series phase versus time for the first resistive member under "Flow" and "No Flow" conditions for a 4-volt input voltage signal.
Figure 10F:
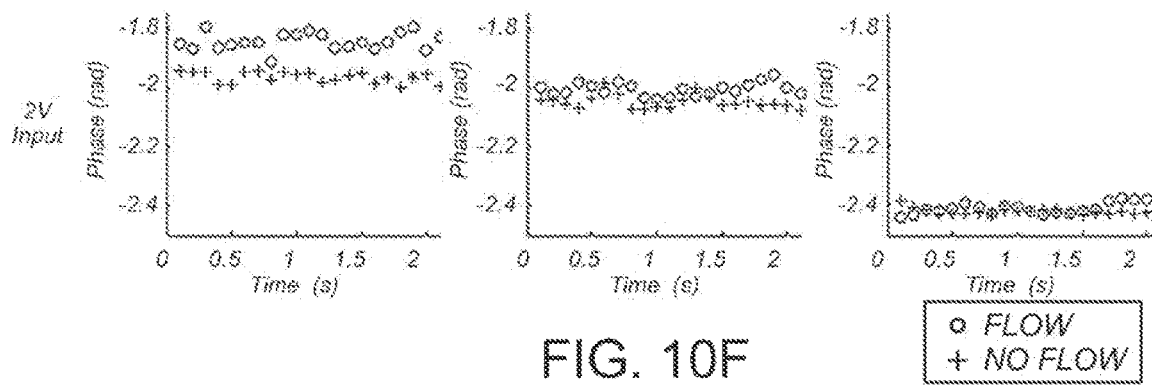

FIGS. 10A, 10B and 10C show graphs or plots of power series magnitude (in volts) versus time for a first one of the resistive members (denominated as elongate member #1, resistive member #4) in response to a variety of input voltage signals with the following pairs of signal characteristics: 8 V, 0.5 Hz; 8 V, 1 Hz; and 8V, 2.5 Hz as shown in FIG. 10A; 4 V, 0.5 Hz; 4V, 1 Hz; and 4 V, 2.5 Hz as shown in FIG. 10B: and 2 V, 0.5 Hz; 2 V, 1 Hz; and 2 V, 2.5 Hz as shown in FIG. 10C. FIGS. 10D, 10E and 10F respectively show graphs or plots of power series phase (in radians) versus time for the first one of the resistive members (denominated as elongate member #1, resistive member #4) in response to a variety of input voltage signals with the following pairs of signal characteristics: 8V, 0.5 Hz; 8 V, 1 Hz; and 8V, 2.5 Hz as shown in FIG. 10D; 4 V, 0.5 Hz; 4 V, 1 Hz; and 4 V, 2.5 Hz as shown in FIG. 10E; and 2 V, 0.5 Hz; 2 V, 1 Hz; and 2 V, 2.5 Hz as shown in FIG. 10F. The results for the Flow conditions are represented by the symbol "o" in each graph or plot while the results for the No Flow conditions are represented by the symbol "+" in each graph or plot. It is evident from the graphs or plots of FIGS. 10A, 10B and 10C that a lack of substantial differentiation exists between the magnitude values corresponding to the Flow conditions and the magnitude values corresponding to the No Flow conditions for this particular resistive member.

However, the plots of FIGS. 10D, 10E and 10F show that a noticeable differentiation exists between the phase values corresponding to the Flow conditions and the phase values corresponding to the No Flow conditions for this particular resistive member for the 1 Hz voltage signals and an even more pronounced differentiation exists between the phase values corresponding to the Flow conditions and the phase values corresponding to the No Flow conditions for this particular resistive member for the 0.5 Hz voltage signals.

Example 2

Figure 11A:
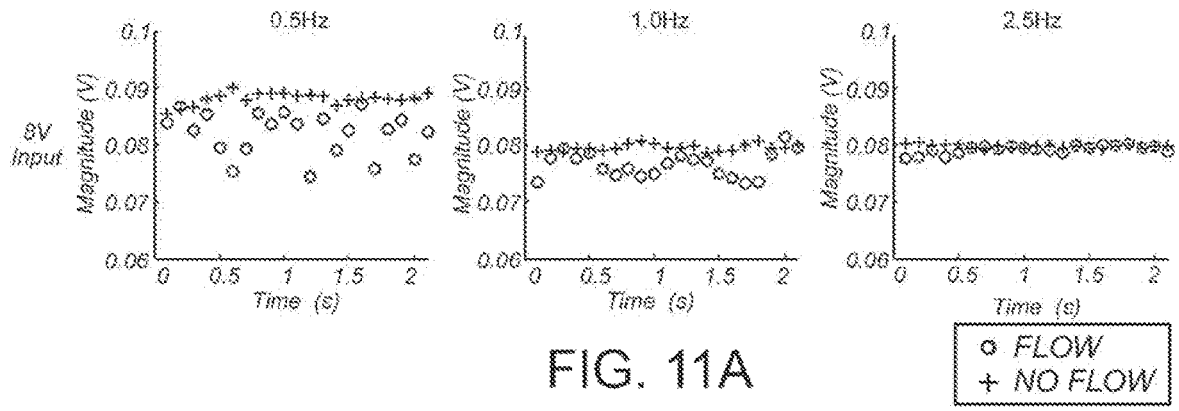
FIG. 11A is a graph or plot of a Fourier power series magnitude versus time for a second resistive member under "Flow" and "No Flow" conditions for an 8-volt input voltage signal.
Figure 11B:
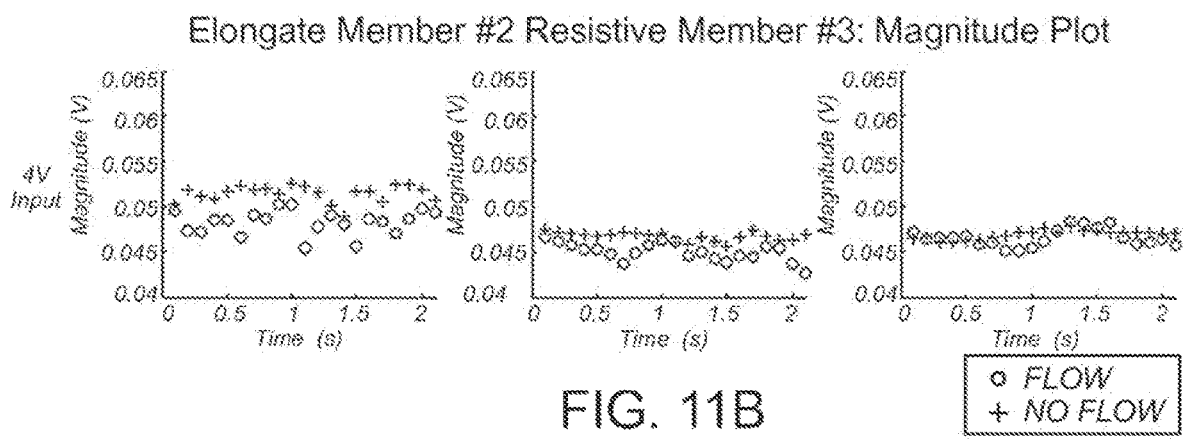
FIG. 11B is a graph or plot of a Fourier power series magnitude versus time for the second resistive member under "Flow" and "No Flow" conditions for a 4-volt input voltage signal.
Figure 11C:
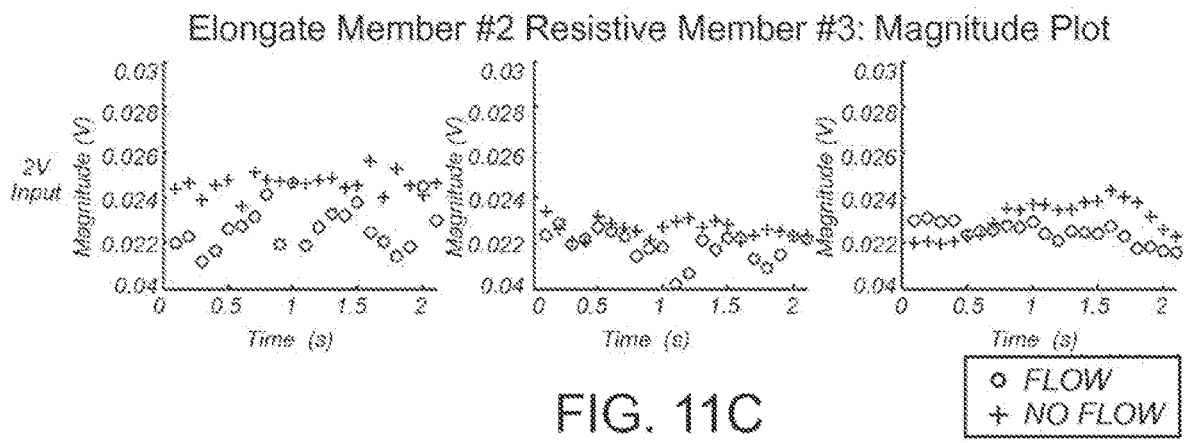
FIG. 11C is a graph or plot of a Fourier power series magnitude versus time for the second resistive member under "flow" and "No Flow" conditions for a 2-volt input voltage signal.
Figure 11D:
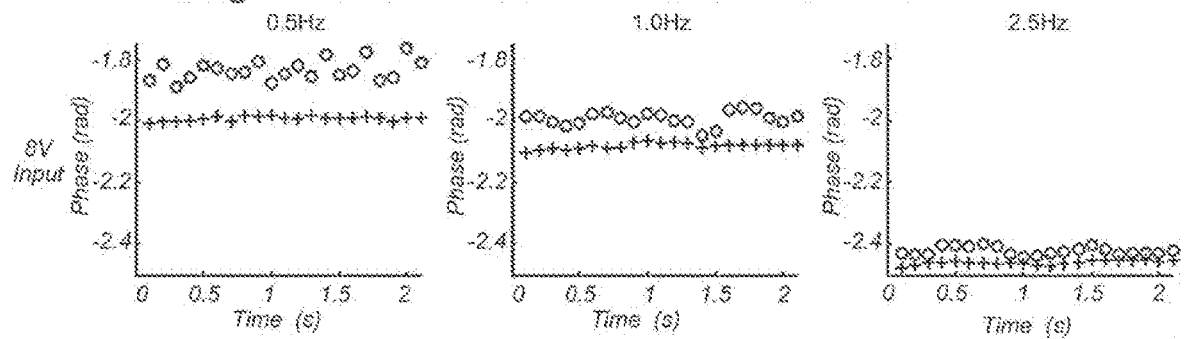
FIG. 11D is a graph or plot of a Fourier power series phase for the second resistive member under "Flow" and "No Flow" conditions for an volt input voltage signal.
Figure 11E:
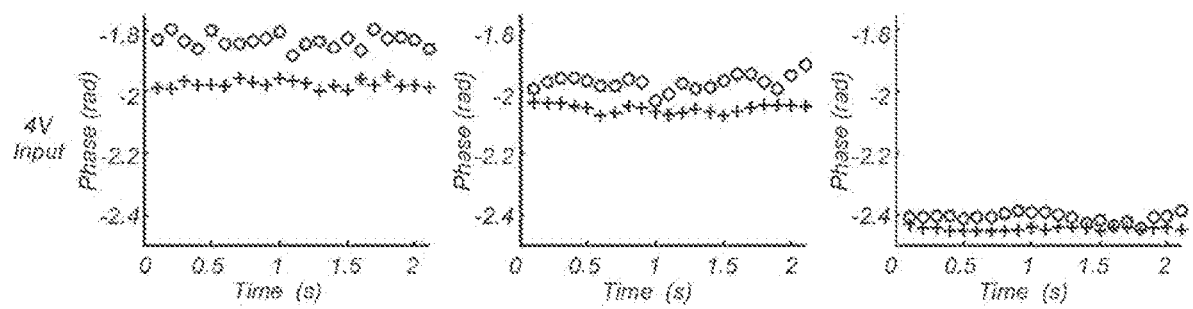
FIG. 11E is a graph or plot of a Fourier power series phase for the second resistive member under "Flow" and "No Flow" conditions for a 4-volt input voltage signal.
Figure 11F:
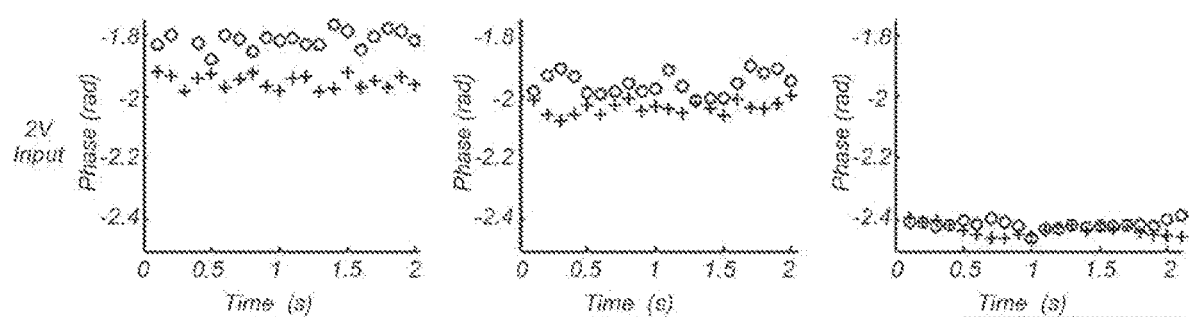
FIG. 11F is a graph or plot of a Fourier power series phase for the second resistive member under "Flow" and "No Flow" conditions for a 2-volt input voltage signal.

FIGS. 11A, 11B and 11C respectively show graphs or plots of power series magnitude (in volts) versus time for a second one of the resistive members (denominated as elongate member #2, resistive member #3) in response to a variety of input voltage signals with the following pairs of signal characteristic: 8 V, 0.5 Hz; 8 V, 1 Hz; and 8 V, 2.5 Hz as shown in FIG. 11A; 4 V, 0.5 Hz; 4 V, 1 Hz; and 4 V, 2.5 Hz as shown in FIG. 11B; and 2 V, 0.5 Hz; 2 V, 1 Hz; and 2 V, 2.5 Hz as shown in FIG. 11C. FIGS. 11D, 11E and 11F respectively show graphs or plots of power series phase (in radians) versus time for the second one of the resistive members (denominated as elongate member #2, resistive member #3) in response to a variety of the input voltage signals with the following pairs of signal characteristic; 8 V, 0.5 Hz; 8 V, 1 Hz; and 8 V, 2.5 Hz as shown in FIG. 11D; 4 V, 0.5 Hz; 4 V, 1 Hz, and 4 V, 2.5 Hz as shown in FIG. 11E; and 2 V, 0.5 Hz; 2 V, 1 Hz; and 2 V, 2.5 Hz as shown in FIG. 11F. The results for the Flow conditions are represented by the symbol "o" in each plot while the results for the No Flow conditions are represented by the symbol "+" in each plot. In a similar manner to that shown in FIGS. 10A, 10B and 10C, the graphs or plots in FIGS. 11A, 11B and 11C also show a lack of substantial differentiation between the magnitude values corresponding to the Flow conditions and the magnitude values corresponding to the No Flow conditions for this particular resistive member. However, the graphs or plots of FIGS. 11D, 11E and 11F show that a noticeable differentiation exists between the phase values corresponding to the Flow conditions and the phase values corresponding to the No Flow conditions for this particular resistive member for the 1 Hz voltage signals and an even more pronounced differentiation exists between the phase values corresponding to the Flow conditions and the phase values corresponding to the No Flow conditions for this particular resistive member for the 0.5 Hz voltage signals.

Figure 12:
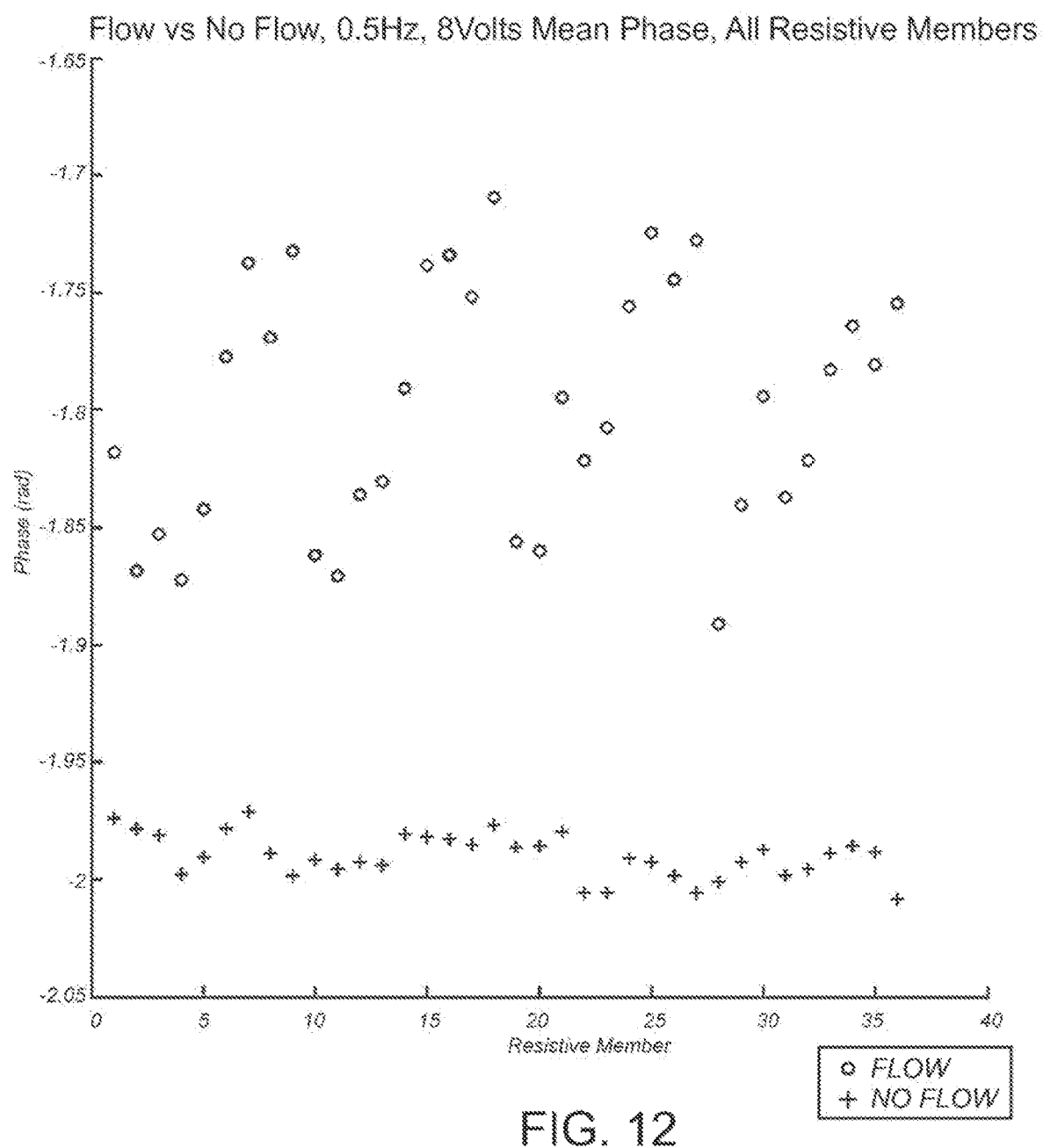
FIG. 12 is a graph or plot for a power series average phase value (radians) for each of a plurality of resistive members including the first resistive member of FIGS. 10A and 10B and the second resistive member of FIGS. 11A and 11B in both the Flow and No Flow conditions.

Similar results were also obtained for other ones of the resistive members. FIG. 12 shows a graph or plot for power series average phase value (in radians) versus time for each of the tested resistive members in both the Flow and No Flow conditions under the influence of or in response to an input voltage signal with 8 V, 0.5 Hz signal characteristics. The results for the Flow conditions are represented by the symbol "o" in each plot while the results for the No Flow conditions are represented by the symbol "+" in each plot. In this graph or plot, the resistive members denominated as #1 through #9 of elongate member #1 are identified by respective numbers 1 through 9 on the x axis. The resistive members denominated as #1 through #9 of elongate member #2 are identified by respective numbers 10 through 18 on the x axis. The resistive members denominated as #1 through #9 of elongate member #3 are identified by respective numbers 19 through 27 on the x axis. The resistive members denominated as #1 through 49 of elongate member #4 are identified by respective numbers 28 through 36 on the x axis. The graph or plot of FIG. 12 shows that a noticeable differentiation exists between the phase values corresponding to the Flow conditions and the phase values corresponding to the No Flow conditions for each of the elements under these input conditions. It is noted that larger phase differences between the Flow and No Flow conditions exist for the "higher" numbered resistive members positioned on each of the tour elongate members indicating that these particular resistive members were positioned to experience greater flow conditions.

While the embodiments disclosed above are described with examples of cardiac mapping, the same or similar embodiments may be used for mapping other bodily organs, for example gastric mapping, bladder mapping, arterial mapping and mapping of any lumen or cavity into which the devices of the present invention may be introduced.

While the embodiments disclosed above are described with examples of cardiac ablation, the same or similar embodiments may be used for ablating other bodily organs or any lumen or cavity into which the devices of the present invention may be introduced.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the invention can be modified, if necessary, to employ systems, circuits and concepts of the various patents, applications and publications to provide yet further embodiments of the invention.

These and other changes can be made to the invention in light of the above-detailed description. In general, in the following claims, the terms used should not be construed to limit the invention to the specific embodiments disclosed in the specification and the claims, but should be construed to include all medical treatment devices in accordance with the claims. Accordingly, the invention is not limited by the disclosure, but instead its scope is to be determined entirely by the following claims.

The invention claimed is:

1. A catheter comprising:
   an expandable structure selectively configurable between a delivery configuration in which the expandable structure is percutaneously deliverable to an intra-cardiac cavity and an expanded configuration in which the expandable structure is sized too large to be percutaneously deliverable to the intra-cardiac cavity; and
   a plurality of transducer elements, each transducer element of the plurality of transducer elements comprising a respective electrode and a respective sensor, at least a portion of each transducer element of the plurality of transducer elements supported by a surface of the expandable structure,
   wherein the at least the portion of each transducer element of the plurality of transducer elements comprises the respective electrode, the respective electrode configured to deliver ablative energy to tissue of a bodily cavity,
   wherein the respective sensor is located between the surface of the expandable structure and the respective electrode; and
   wherein, for each transducer element of the plurality of transducer elements, the respective electrode overlies the respective sensor.

2. The catheter of claim 1, wherein the surface of the expandable structure is a front surface of the expandable structure configured to face outwardly from the expandable structure in a state in which the expandable structure is in the expanded configuration.

3. The catheter of claim 1, wherein, for each transducer element of the plurality of transducer elements, the respective electrode is located further from a front surface of the expandable structure than the respective sensor, the front surface configured to face outwardly away from the expandable structure in a state in which the expandable structure is in the expanded configuration.

4. The catheter of claim 1, wherein the surface of the expandable structure is configured to move to increase a size of the expandable structure when the expandable structure moves from the delivery configuration toward the expanded configuration.

5. The catheter of claim 1, wherein the surface of the expandable structure is configured to move outwardly away from an interior of the expandable structure as the expandable structure moves from the delivery configuration toward the expanded configuration.

6. The catheter of claim 1, wherein a respective portion of each respective sensor is supported by the surface of the expandable structure.

7. The catheter of claim 1, wherein, for each transducer element of the plurality of transducer elements, the respective electrode and the respective sensor are integrally formed.

8. The catheter of claim 1, wherein, for each transducer element of the plurality of transducer elements, the respective electrode and the respective sensor are integrally formed as part of a flexible circuit structure.

9. The catheter of claim 1, wherein each transducer element of the plurality of transducer elements comprises a plurality of electrically conductive layers and a plurality of electrically insulative layers, the plurality of electrically conductive layers interleaved with the plurality of electrically insulative layers.

10. The catheter of claim 9, wherein, for a first transducer element of the plurality of transducer elements, the respective sensor is located between two electrically insulative layers of the plurality of electrically insulative layers of the first transducer element.

11. The catheter of claim 9, wherein, for a first transducer element of the plurality of transducer elements, an electrically insulative layer of the plurality of electrically insulative layers of the first transducer element is positioned between the respective electrode and the respective sensor of the first transducer element.

12. The catheter of claim 9, wherein, for a first transducer element of the plurality of transducer elements, at least two electrically insulative layers of the plurality of electrically insulative layers of the first transducer element are located between the respective sensor of the first transducer element and the surface of the expandable structure.

13. The catheter of claim 12, wherein at least one electrically conductive layer of the plurality of electrically conductive layers of the first transducer element is located between the at least two electrically insulative layers of the plurality of electrically insulative layers of the first transducer element.

14. The catheter of claim 1, wherein the respective sensor of a first transducer element of the plurality of transducer elements is a temperature sensor.

15. The catheter of claim 1, wherein the respective sensor of a first transducer element of the plurality of transducer elements comprises a resistive member.

16. The catheter of claim 1, wherein the respective electrode of at least a first transducer element of the plurality of transducer elements is configured to deliver ablative energy comprising radio-frequency energy.

17. The catheter of claim 1, wherein the expandable structure comprises a plurality of elongate members, and wherein the surface of the expandable structure is provided by a surface of a particular elongate member of the plurality of elongate members.

18. The catheter of claim 17, wherein the surface of the particular elongate member of the plurality of elongate members is a front surface of the particular elongate member configured to face outwardly away from an interior volume encompassed by the expandable structure in a state in which the expandable structure is in the expanded configuration.

19. The catheter of claim 1, wherein the expandable structure comprises an inflatable member.

20. The catheter of claim 1, wherein the plurality of transducer elements is integrated into a flexible circuit structure located on the expandable structure.

21. The catheter of claim 1, wherein the expandable structure is an expandable metallic frame.

22. The catheter of claim 21, wherein the plurality of transducer elements is integrated into a flexible circuit structure located on the expandable metallic frame.

* * * * *